(12) United States Patent
Moutafis et al.

(10) Patent No.: US 8,529,498 B2
(45) Date of Patent: Sep. 10, 2013

(54) LIQUID JET SURGICAL INSTRUMENTS INCORPORATING CHANNEL OPENINGS ALIGNED ALONG THE JET BEAM

(75) Inventors: Timothy E. Moutafis, Gloucester, MA (US); Donald C. Freeman, Jr., Burlington, MA (US); Edward J. Bromander, Tewksbury, MA (US)

(73) Assignee: Smith & Nephew, Inc., London ( * ) Notice: Subject to any disclaimer, the term of this patent is extended or adjusted under 35 U.S.C. 154(b) by 1105 days.

(21) Appl. No.: 12/207,282

(22) Filed: Sep. 9, 2008

(65) Prior Publication Data

US 2009/0076440 A1    Mar. 19, 2009

Related U.S. Application Data

(62) Division of application No. 10/302,766, filed on Nov. 21, 2002, now Pat. No. 7,431,711.

(60) Provisional application No. 60/332,156, filed on Nov. 21, 2001.

(51) Int. Cl.
*A61M 1/00* (2006.01)

(52) U.S. Cl.
USPC .......................................................... 604/35

(58) Field of Classification Search
USPC ................. 604/20, 22, 35, 58, 61, 68, 69, 70, 604/73, 257, 264, 43; 606/45, 167, 180
See application file for complete search history.

(56) References Cited

U.S. PATENT DOCUMENTS

| | | | |
|---|---|---|---|
| 1,889,425 A | 11/1932 | Sorensen | |
| 1,902,418 A | 3/1933 | Pilgrim | |
| 3,565,062 A | 2/1971 | Kuris | |
| 3,590,813 A | 7/1971 | Roszyk | |
| 3,818,913 A | 6/1974 | Wallach | |
| 3,930,505 A | 1/1976 | Wallach | |
| 4,024,866 A | 5/1977 | Wallach | |

(Continued)

FOREIGN PATENT DOCUMENTS

| | | |
|---|---|---|
| DE | 4018736 A1 | 1/1992 |
| EP | 0175096 B1 | 3/1986 |

(Continued)

OTHER PUBLICATIONS

Canadian Office Action for Application No. 2,495,911, dated Feb. 9, 2009.

(Continued)

*Primary Examiner* — Kevin C Sirmons
*Assistant Examiner* — Imani Hayman
(74) *Attorney, Agent, or Firm* — McCarter & English, LLP; David R. Burns

(57) ABSTRACT

Certain embodiments of the surgical instruments provided according to the invention utilize a channel positioned adjacent to and downstream of a liquid jet-forming nozzle such that at least a portion of the liquid jet passes at least one of within the channel and adjacent to and along the length of at least a portion of a longitudinally-oriented opening in the channel, when the instrument is in operation. The use of such channels in certain embodiments of the inventive surgical instruments can enable the instruments to provide enhanced control over the depth and degree of cutting and/or ablation of tissue; and/or can provide improved and enhanced functionality for cleaning, debriding, and/or trimming and cutting a tissue/surface; and/or can provide longer effective liquid jet beam cutting/ablation lengths by reducing the degree of dispersion of the jet along its length.

14 Claims, 10 Drawing Sheets

(56) References Cited

U.S. PATENT DOCUMENTS

| | | |
|---|---|---|
| 4,111,490 A | 9/1978 | Liesveld |
| 4,137,804 A | 2/1979 | Gerber et al. |
| 4,245,624 A | 1/1981 | Komiya |
| 4,282,867 A | 8/1981 | Du Toit et al. |
| 4,294,251 A | 10/1981 | Greenwald et al. |
| 4,368,734 A | 1/1983 | Banko |
| 4,435,902 A | 3/1984 | Mercer et al. |
| 4,560,373 A | 12/1985 | Sugino et al. |
| 4,583,531 A | 4/1986 | Mattchen |
| 4,637,551 A | 1/1987 | Seeger, Jr. et al. |
| 4,690,672 A | 9/1987 | Veltrup et al. |
| 4,694,828 A | 9/1987 | Eichenbaum |
| 4,715,848 A | 12/1987 | Beroza |
| 4,735,620 A | 4/1988 | Ruiz |
| 4,798,339 A | 1/1989 | Sugino et al. |
| 4,827,679 A | 5/1989 | Earle, III |
| 4,839,492 A | 6/1989 | Bouchier et al. |
| 4,898,574 A | 2/1990 | Uchiyama et al. |
| 4,913,698 A | 4/1990 | Ito et al. |
| 4,935,006 A | 6/1990 | Hasson |
| 4,937,985 A | 7/1990 | Boers et al. |
| 5,002,546 A | 3/1991 | Romano |
| 5,018,670 A | 5/1991 | Chalmers |
| 5,027,792 A | 7/1991 | Meyer |
| 5,037,431 A | 8/1991 | Summers et al. |
| 5,052,624 A | 10/1991 | Boers et al. |
| 5,057,098 A | 10/1991 | Zelman |
| 5,074,862 A | 12/1991 | Rausis et al. |
| 5,111,652 A | 5/1992 | Andre et al. |
| 5,125,582 A | 6/1992 | Surjaatmadja et al. |
| 5,135,482 A | 8/1992 | Neracher et al. |
| 5,135,484 A | 8/1992 | Wright |
| 5,162,016 A | 11/1992 | Malloy |
| 5,186,714 A | 2/1993 | Boudreault et al. |
| 5,195,958 A | 3/1993 | Phillips |
| 5,205,779 A | 4/1993 | O'Brien et al. |
| 5,217,465 A | 6/1993 | Steppe |
| 5,230,704 A | 7/1993 | Moberg et al. |
| 5,242,449 A | 9/1993 | Zaleski |
| 5,250,065 A | 10/1993 | Clement et al. |
| 5,259,842 A | 11/1993 | Plechinger et al. |
| 5,300,022 A | 4/1994 | Klapper et al. |
| 5,314,375 A | 5/1994 | O'Brien et al. |
| 5,318,518 A | 6/1994 | Plechinger et al. |
| 5,320,599 A | 6/1994 | Griep et al. |
| 5,322,504 A | 6/1994 | Doherty et al. |
| 5,370,609 A | 12/1994 | Drasler et al. |
| 5,395,315 A | 3/1995 | Griep |
| 5,441,482 A | 8/1995 | Clague et al. |
| 5,449,369 A | 9/1995 | Imran |
| 5,453,088 A | 9/1995 | Boudewijn et al. |
| 5,454,827 A | 10/1995 | Aust et al. |
| 5,468,028 A | 11/1995 | Olson |
| 5,476,450 A | 12/1995 | Ruggio |
| 5,496,267 A | 3/1996 | Drasler et al. |
| 5,505,729 A | 4/1996 | Rau et al. |
| 5,524,821 A | 6/1996 | Yie et al. |
| 5,527,330 A | 6/1996 | Tovey |
| 5,551,448 A | 9/1996 | Matula et al. |
| 5,556,406 A | 9/1996 | Gordon et al. |
| 5,562,640 A | 10/1996 | McCabe et al. |
| 5,562,692 A | 10/1996 | Bair |
| 5,591,184 A | 1/1997 | McDonnell et al. |
| 5,607,391 A | 3/1997 | Klinger et al. |
| 5,620,414 A | 4/1997 | Campbell, Jr. |
| 5,643,299 A | 7/1997 | Bair |
| 5,674,226 A | 10/1997 | Doherty et al. |
| 5,697,281 A | 12/1997 | Eggers et al. |
| 5,709,697 A | 1/1998 | Ratcliff et al. |
| 5,713,849 A | 2/1998 | Bosma et al. |
| 5,713,851 A | 2/1998 | Boudewijn et al. |
| 5,713,878 A | 2/1998 | Moutafis et al. |
| 5,735,815 A | 4/1998 | Bair |
| 5,782,795 A | 7/1998 | Bays |
| 5,785,675 A | 7/1998 | Drasler et al. |
| 5,788,667 A | 8/1998 | Stoller |
| 5,792,167 A | 8/1998 | Kablik et al. |
| 5,853,384 A | 12/1998 | Bair |
| 5,871,462 A | 2/1999 | Yoder et al. |
| 5,944,686 A | 8/1999 | Patterson et al. |
| 5,947,988 A | 9/1999 | Smith |
| 6,045,564 A | 4/2000 | Walen |
| 6,066,150 A | 5/2000 | Gonon et al. |
| 6,083,189 A | 7/2000 | Gonon et al. |
| 6,096,001 A | 8/2000 | Drasler et al. |
| 6,099,514 A | 8/2000 | Sharkey et al. |
| 6,135,977 A | 10/2000 | Drasler et al. |
| 6,149,622 A | 11/2000 | Marie et al. |
| 6,216,573 B1 | 4/2001 | Moutafis et al. |
| 6,280,302 B1 | 8/2001 | Hashish et al. |
| 6,322,533 B1 | 11/2001 | Gonon et al. |
| 6,375,635 B1 | 4/2002 | Moutafis et al. |
| 6,402,715 B2 | 6/2002 | Manhes et al. |
| 6,419,654 B1 | 7/2002 | Kadan |
| 6,451,017 B1 | 9/2002 | Moutafis et al. |
| 6,464,567 B2 | 10/2002 | Hashish et al. |
| 6,491,660 B2 | 12/2002 | Guo et al. |
| 6,508,823 B1 | 1/2003 | Gonon et al. |
| 6,511,493 B1 | 1/2003 | Moutafis et al. |
| 6,544,220 B2 | 4/2003 | Shuman et al. |
| 6,669,710 B2 | 12/2003 | Moutafis et al. |
| 2001/0002562 A1 | 6/2001 | Moutafis et al. |
| 2002/0111579 A1 | 8/2002 | Moutafis et al. |
| 2002/0176788 A1 | 11/2002 | Moutafis et al. |
| 2002/0177802 A1 | 11/2002 | Moutafis et al. |
| 2003/0009166 A1 | 1/2003 | Moutafis et al. |
| 2003/0040763 A1 | 2/2003 | Moutafis et al. |
| 2003/0055404 A1 | 3/2003 | Moutafis |
| 2003/0083681 A1 | 5/2003 | Moutafis et al. |
| 2003/0088259 A1 | 5/2003 | Staid et al. |
| 2004/0023021 A1 | 2/2004 | Hisashi et al. |
| 2004/0228736 A1 | 11/2004 | Moutafis et al. |
| 2004/0234380 A1 | 11/2004 | Moutafis et al. |
| 2004/0243157 A1 | 12/2004 | Connor et al. |

FOREIGN PATENT DOCUMENTS

| | | |
|---|---|---|
| EP | 0253478 B1 | 1/1988 |
| EP | 0258901 A2 | 3/1988 |
| EP | 0280972 A1 | 9/1988 |
| EP | 0367855 A1 | 5/1990 |
| EP | 0411170 A1 | 2/1991 |
| EP | 0442579 A1 | 8/1991 |
| EP | 0470781 A1 | 2/1992 |
| EP | 0485133 A1 | 5/1992 |
| EP | 0489496 A1 | 6/1992 |
| EP | 0551920 B1 | 7/1993 |
| EP | 0620016 A1 | 10/1994 |
| EP | 0636345 A1 | 2/1995 |
| EP | 0637453 A1 | 2/1995 |
| EP | 0693295 A1 | 1/1996 |
| EP | 0737450 A1 | 10/1996 |
| EP | 0806213 A1 | 11/1997 |
| FR | 2779934 A1 | 12/1999 |
| FR | 2779935 A1 | 12/1999 |
| WO | WO-90/05493 A1 | 5/1990 |
| WO | WO-94/10917 A1 | 5/1994 |
| WO | WO-94/28807 A1 | 12/1994 |
| WO | WO-96/24299 A1 | 8/1996 |
| WO | WO-96/39954 A1 | 12/1996 |
| WO | WO-96/40476 A1 | 12/1996 |
| WO | WO-97/03713 A1 | 2/1997 |
| WO | WO-97/49441 A1 | 12/1997 |
| WO | WO-99/33510 A1 | 7/1999 |
| WO | WO-99/65407 A1 | 12/1999 |
| WO | WO-99/65408 A1 | 12/1999 |
| WO | WO-99/66848 A1 | 12/1999 |
| WO | WO-00/69348 A1 | 11/2000 |
| WO | WO-01/50965 A2 | 7/2001 |
| WO | WO-01/50966 A2 | 7/2001 |
| WO | WO-02/095234 A1 | 11/2002 |
| WO | WO-03/013645 A1 | 2/2003 |
| WO | WO-03/024340 A2 | 3/2003 |
| WO | WO-2004/069064 A2 | 8/2004 |

OTHER PUBLICATIONS

Aeikens, B., "Cracking of Ureter Calculi by High Speed Water Jet Pulses," *8th International Symposium on Jet Cutting Technology*, Paper 15, pp. 157-166, Sep. 9-11 1986.

Baer et al., "Hepatic Surgery Facilitated by a New Jet Dissector," *HPB Surgery*, vol. 4:137-146 (1991).

Baer et al., "Jet-Cutting—an Alternative to the Ultrasonic Aspirator?" *Chirurg*, vol. 61:735 (1990).

Baer et al., "New water-jet dissector: initial experience in hepatic surgery," *Br. J. Surg.*, vol. 78:502-503 (1991).

Baer et al., "Subtotal hepatectomy: a new procedure based on the inferior right hepatic vein," *Br. J. Surg.*, vol. 78:1221-1222 (1991).

Baer et al., "Water-jet dissection in hepatic surgery," *Minimally Invasive Therapy*, vol. 1:169-172 (1992).

Beard, J., "Water jet puts surgeons at the cutting edge," *New Scientist*, (1994).

Bücker, Arno et al., "Comparative in Vitro Study of Two Percutaneous Hydrodynamic Thrombectomy Systems," *Journal of Vascular and Interventional Radiology*, vol. 7(3):445-449 (1996).

Douek et al., "Functional Properties of a Prototype Rheolytic Catheter for Percutaneous Thrombectomy In Vitro Investigations," *Investigative Radiology*, vol. 29(5):547-552 (1994).

Drasler et al., "A Rheolytic system for Percutaneous Coronary and Peripheral Plaque Removal," *Angiology—The Journal of Vascular Diseases*, vol. 42(2):90-98 (1991).

Drasler et al., "Rheolytic Catheter for Percutaneous Removal of Thrombus," *Radiology*, vol. 182:263-267 (1992).

Field J.E, "The physics of liquid impact, shock wave interactions with cavities and the implications to shock wave lithotripsy," *Phys. Med. Biol.*, vol. 36(11):1475-1484 (1991).

Giraud et al., "Bone cutting," *Clin. Phys. Physiol. Meas.*, vol. 12(1):1-19 (1991).

Hata et al., "Liver Resection in Children, Using a Water-Jet," *Journal of Pediatric Surgery*, vol. 29(5):648-650 (1994).

Izumi et al., "Hepatic Resection Using a WAter Jet Dissector," *Surgery Today Jpn. J. Surg.*, vol. 23:31-35 (1993).

Jessen et al., "Endoscopic Jet Cutting of Human Gallstones," *7th Annual Symposium on Jet Cutting Technology*, Paper D4, pp. 211-220 (1984).

Jessen et al., "Endoscopic Jet-Cutting A New Method for Stone Destruction in the Common Bile Duct," *6th Internal Symposium on Jet Cutting Technology*, Paper Bl, pp. 39-52 (1982).

Kobayashi et al., "Experimental Study on Water Jet Angioplasty," *Vascular Surgery—International Conference*, vol. 2:626-631 (1993).

Müller-Hülsbeck et al., "Rheolytic Thrombectomy of an Acutely Thrombosed Transjugular Intrahepatic Portosystemic Stent Shunt," *CardioVasc. Intervent. Radiol.*, vol. 19:294-297 (1996).

Overbosch et al., "Occluded Hemodialysis Shunts: Dutch Multicenter Experience with the Hydrolyser Catheter," *Radiology*, vol. 201 (2):485-488 (1996).

Papachristou et al., "Resection of the liver with a water jet," *Br. J. Surg.*, vol. 69:93-94 (1982).

Persson et al., "Transection of the Liver with a Water Jet," *Surgery, Gynecology & Obstetrics*, vol. 168:267-268 (1989).

Reekers et al., "Catheter for Percutaneous Thrombectomy: First Clinical Experience," *Radiology*, vol. 188(3):871-874 (1993).

Schob et al., "Experimental laparoscopic liver resection with a multimodal water jet dissector," *British Journal of Surgery*, vol. 82:392-393 (1995).

Schob et al., "The Multimodal Water Jet Dissector—a Technology for Laparoscopic Liver Surgery," *End. Surg.*, vol. 2:311-314 (1994).

Shimi, S.M., "Dissection techniques in laparoscopic surgery: a review," *J.R. Coll. Surg. Edinb.*, vol. 40:249-259 (1995).

Spence, R.K., "Emerging Trends in Surgical Blood Transfusion," *Seminars in Hematology*, vol. 3(3):48-53 (1997).

Summers et al., "The Impact of Waterjets on Human Flesh," *9th International Symposium on Jet Cutting Technology*, Paper H4, pp. 423-433 (1988).

Terzis et al., "A New System for Cutting Brain Tissue Preserving Vessels: water jet cutting," *British Journal of Neurosurgery*, vol. 3:361-366 (1989).

Truchot et al., "Development of a Cryogenic Waterjet Technique for Biomaterial Processing Applications," *6th American Water Jet Conference*, Paper 35:473-480 (1991).

Uchino et al., "Surgical Cutting of the Liver by Water Jet," *9th International Symposium on Jet Cutting Technology*, Poster 1, pp. 629-639 (1988).

Van Ommen et al., "Removal of Thrombus from Aortocoronary Bypass Grafts and Coronary Arteries Using the 6Fr Hydrolyser," *The American Journal of Cardiology*, vol. 79(8):1012-1016 (1997).

Vijay, "A Critical Examination of the Use of Water Jets for Medical Applications," *5th American Water Jet Conference*, Paper-Communication 42, pp. 425-448 (1989).

Water Jet Dissector, Hepatotom.RTM. Supersonic Microjet Dissector Brochure, Medical Exports AG.

Zhong et al., "Propagation of shock waves in elastic solids caused by cavitation microjet impact. II: Application in extracorporeal shock wave lithotripsy," *J. Acoust. Soc. Am.*, vol. 94(1):29-36 (1993).

Communication Pursuant to Article 96(2) EPC dated Jun. 9, 2006 for corresponding European Application No. 02 799 196.7.

Communication from Australian Patent Office dated Mar. 9, 2006 for corresponding Australian Application No. 2002364122.

Communication Pursuant to Article 96(2) EPC dated Nov. 18, 2005 for corresponding European Application No. 02 799 196.7-1265.

Communication Pursuant to Article 96(2) EPC dated Jun. 28, 2005 for corresponding European Application No. 02799196.7-1265.

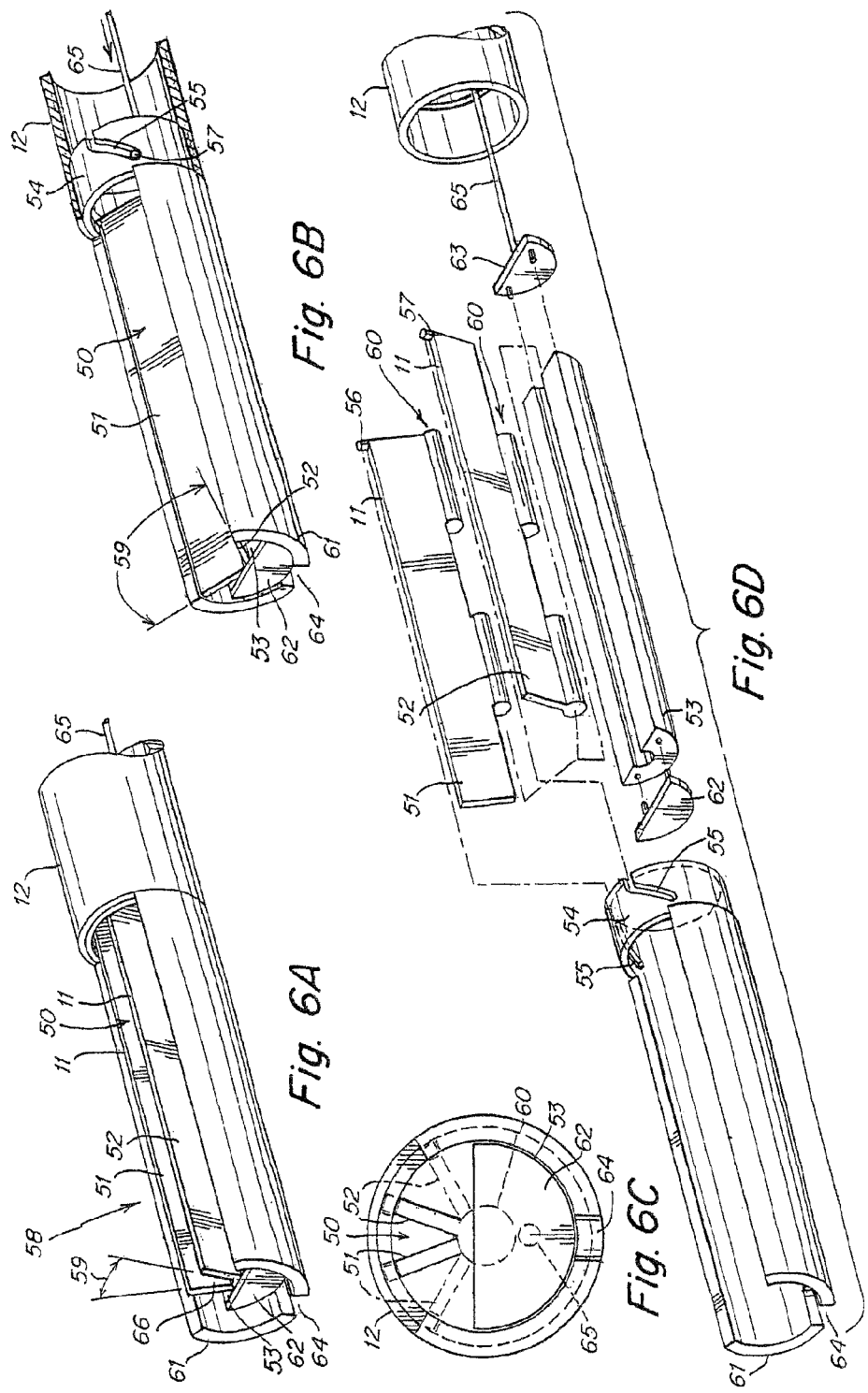

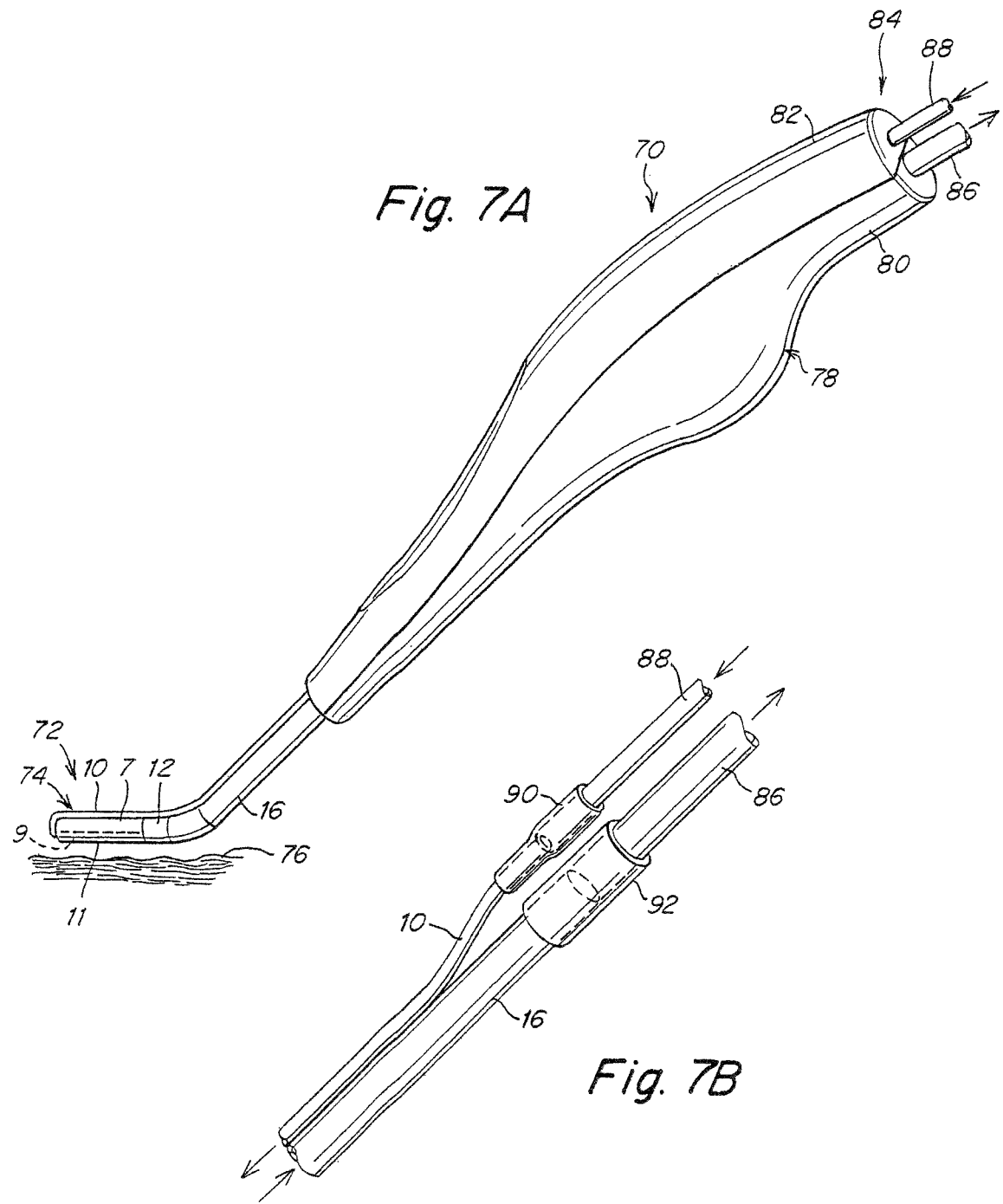

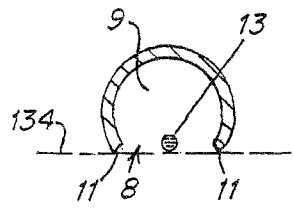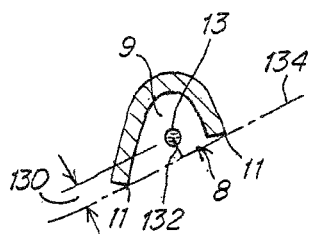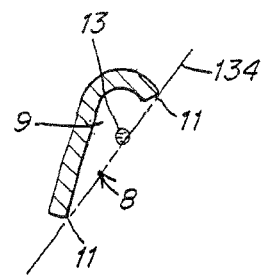
Fig. 9A    Fig. 9B    Fig. 9C
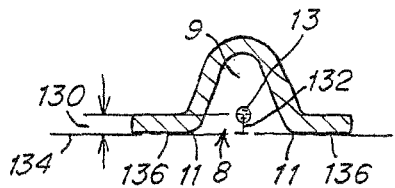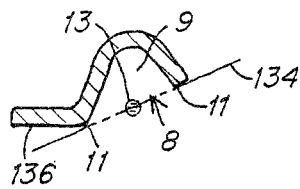
Fig. 9D    Fig. 9E
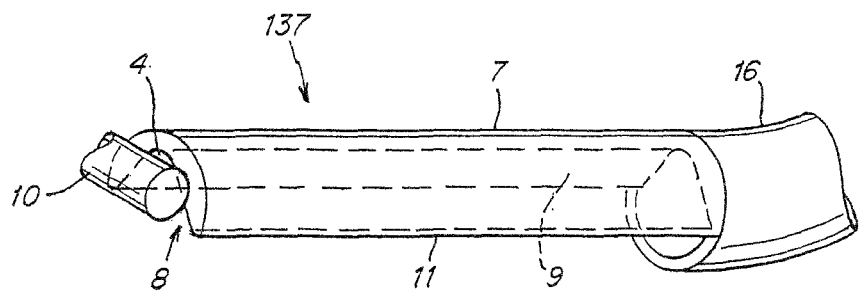
Fig. 10A
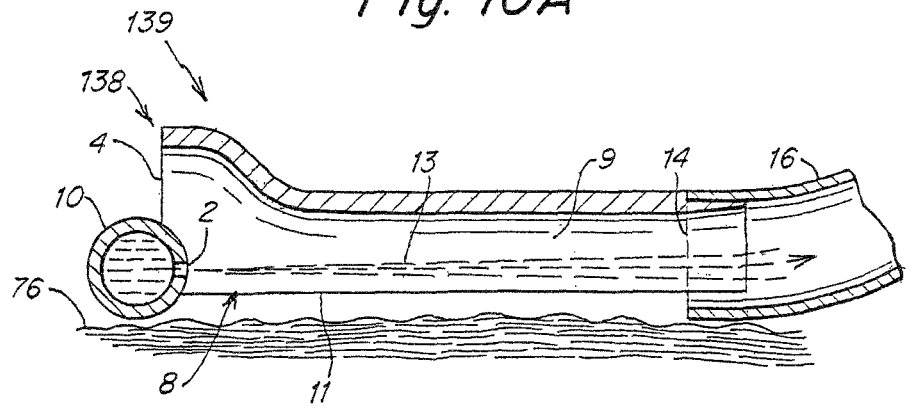
Fig. 10B

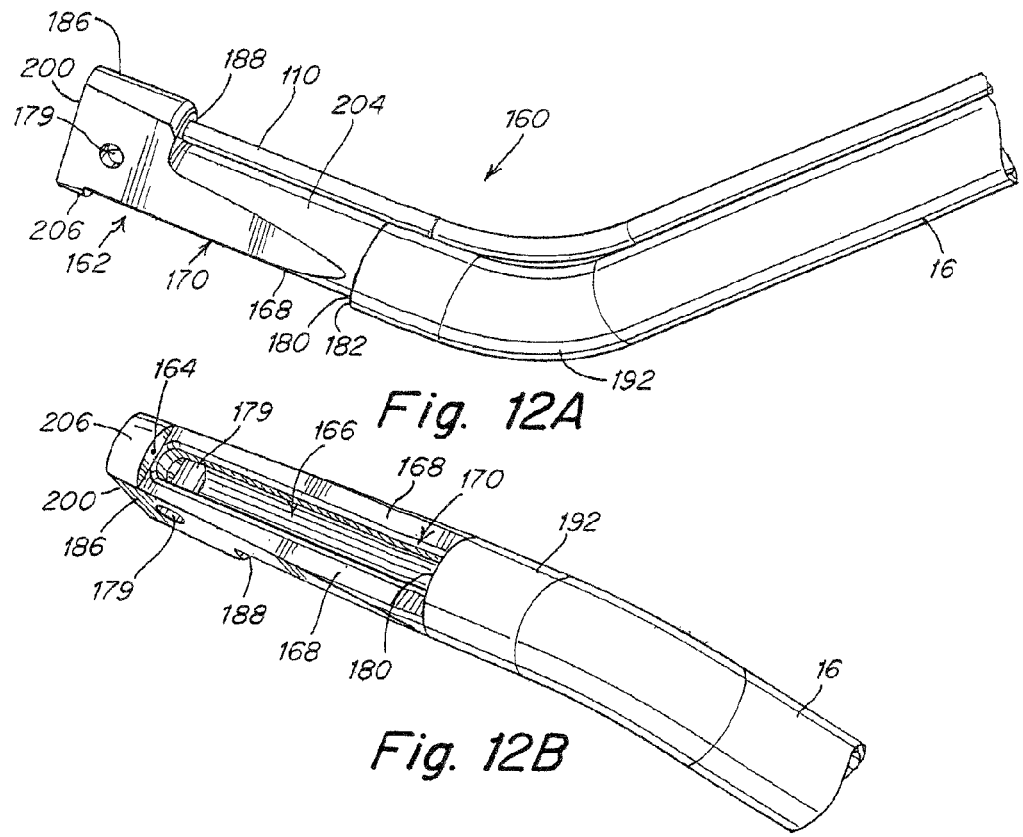
Fig. 12A
Fig. 12B
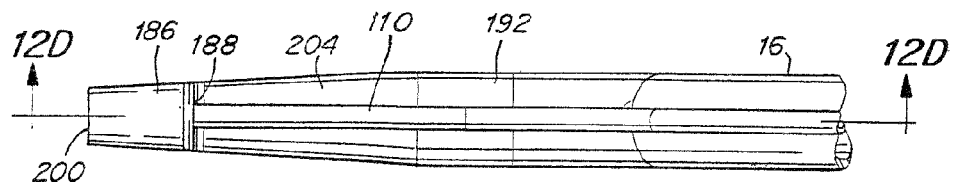
Fig. 12C
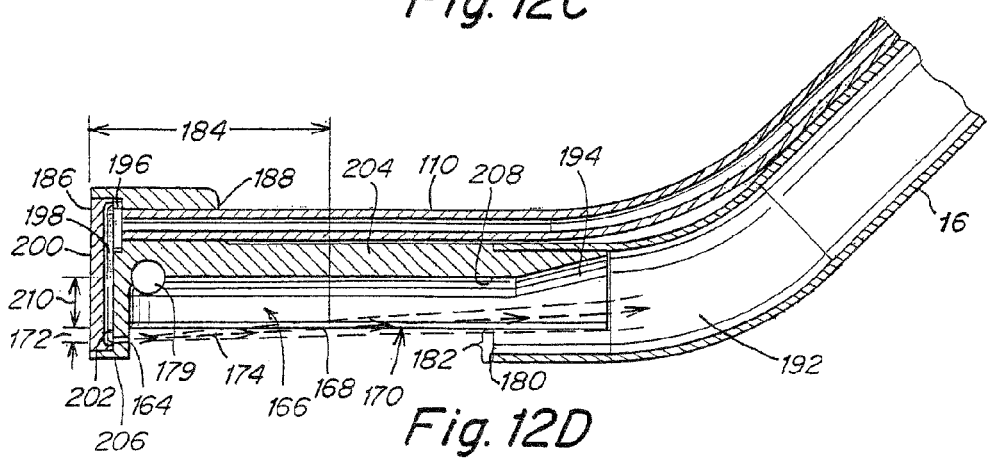
Fig. 12D

LIQUID JET SURGICAL INSTRUMENTS INCORPORATING CHANNEL OPENINGS ALIGNED ALONG THE JET BEAM

RELATED APPLICATIONS

This non-provisional application is a divisional application of U.S. application Ser. No. 10/302,766, filed Nov. 21, 2002 now U.S. Pat. No. 7,431,711, which claims the benefit under Title 35, U.S.C. §119(e) of U.S. provisional application Ser. No. 60/332,156, filed Nov. 21, 2001, the entire content of each application is incorporated herein by reference.

FIELD OF THE INVENTION

This invention relates to liquid jet-forming surgical instruments for cutting, ablating, lavage, and similar treatments of a tissue of a patient during a surgical or medical procedure.

BACKGROUND

Traditionally, many surgical procedures for both open surgery and minimally invasive surgery (i.e., endoscopic, laparoscopic, or arthroscopic surgical procedures) have utilized surgical tools such as scalpels, scrapers, blunt dissectors, lasers, electrosurgical devices, etc., which can have poor tissue differentiating capability, which may easily cause inadvertent damage to tissue surrounding a surgical treatment site, and which do not typically provide for an ability to precisely control a depth of cutting and/or tissue ablation with the instrument and/or effectively provide for evacuation from the treatment site of cut/ablated tissue. Many such surgical procedures can entail more extensive trauma to the patient and/or require longer operating procedures, with associated problems of long recovery periods and potential complication, than is desirable.

Instruments that employ liquid jets have also been utilized in surgical procedures for cutting and ablating tissue. Such instruments can have certain advantages over the above-mentioned traditional surgical instruments for performing surgical and medical procedures. For example, the cutting or ablating power of the liquid jet may be adjusted or controlled by an operator of the instrument, for example by varying the pressure of the liquid supplied to form the jet, to allow for improved tissue differentiation and to reduce inadvertent damage to surrounding tissues when cutting or ablating the target tissue. When operated at lower liquid pressures, the instruments can be utilized for lavage and/or debridement of tissue, without substantial cutting. A variety of such liquid jet surgical instruments for performing open surgical procedures, minimally invasive surgical procedures, and surgical procedures performed on an external portion of the body of a patient (e.g., wound cleansing or skin debridement) are known in the art. Several such instruments are described in the Applicants' U.S. Pat. No. 5,944,686, issued Aug. 31, 1999, U.S. Pat. No. 6,375,635, issued Apr. 23, 2002, and U.S. Pat. No. 6,451,017, issued Sep. 17, 2002, each hereby incorporated by reference.

Several factors can be important to the functional performance of a liquid jet instrument used for surgical procedures or other medical applications. In many surgical or medical procedures, it is desirable to be able to control or select the depth to which a surface of a tissue is cut or ablated with a surgical instrument. In addition, in some surgical and medical procedures (e.g., wound cleansing) it can be desirable to perform effective cleaning and lavage of a tissue surface and/or selective removal of contamination and/or necrotic tissue from such surface without substantial cutting or ablation of healthy tissue. While many of the above-mentioned prior art surgical instruments, and especially liquid jet-based surgical instruments have utility for performing such surgical and medical procedures, there remains a need in the art for surgical instruments, especially liquid jet-based surgical instruments, providing enhanced control over the degree and extent of cutting and/or ablation with the instrument. The present invention provides, in certain embodiments, such improved surgical liquid jet instruments, and further provides methods for their construction and use in a variety of surgical procedures.

SUMMARY OF THE INVENTION

Certain embodiments of the present invention provide a series of surgical instruments utilizing liquid jets for cutting, ablating, debriding, washing, etc., tissues and/or other materials from the interior and/or external surface of the body of a patient. Certain embodiments of the liquid jet surgical instruments provided according to the invention utilize a channel positioned adjacent to and downstream of a liquid jet-forming nozzle such that at least a portion of the liquid jet passes at least one of within the channel and adjacent to and along the length of at least a portion of a longitudinally-oriented opening in the channel, when the instrument is in operation. As explained in more detail below, the use of such channels in certain embodiments of the inventive liquid jet surgical instruments can enable the instruments to provide enhanced control over the depth and degree of cutting and/or ablation of tissue; and/or can provide improved and enhanced functionality for cleaning, debriding, and/or trimming and cutting a tissue surface; and/or can provide longer effective liquid jet beam cutting/ablation lengths by reducing the degree of dispersion of the jet along its length, especially for instruments utilized in a surrounding gaseous environment.

As described below, certain embodiments of the liquid jet surgical instruments provided according to the invention can be utilized for a wide variety of surgical and medical procedures both within the body of a patient (e.g., in open surgical procedures, laparoscopic, endoscopic or arthroscopic surgical procedures), where the liquid jet is typically formed in a surrounding liquid environment, as well as on an external body surface of the patient (e.g., on the skin), where the liquid jet is typically surrounded by a gaseous (e.g., air) environment. In many embodiments, the liquid jet surgical instruments described herein can comprise modified versions of the liquid jet surgical hand pieces disclosed and described in detail in Applicants' issued U.S. Pat. No. 6,375,635. In fact, a wide variety of operating and design parameters, configurations, and design considerations for constructing and utilizing liquid jet surgical instruments in surgical and medical applications are discussed in detail in the above-mentioned U.S. Pat. No. 6,375,635. Such parameters, configurations, and considerations disclosed in Applicants' U.S. Pat. No. 6,375,635 can be, in many cases, applicable to and useful for practicing many aspects of the current invention (except as otherwise noted or modified herein).

As noted above, certain embodiments of the instruments disclosed herein can be provided with functionality not present in typical prior art liquid jet surgical instruments. In certain embodiments, the liquid jet surgical instrument provided according to the invention include a liquid jet-forming nozzle constructed and positioned to direct a liquid jet tangentially, and in some embodiments, essentially parallel to the surface of the tissue of a patient to be treated with the instrument. In such embodiments, when the liquid jet beam and/or the surrounding fluid entrained by the liquid jet beam encounters tissue, the tissue can be macerated, cut, stripped, delaminated, debrided, and/or washed by the jet beam and/or the entrained fluid. (See U.S. Pat. No. 6,375,635 for additional explanation and detail.) As mentioned above, and as discussed in more detail in U.S. Pat. No. 6,375,635, ambient fluid present at the operative site in which the liquid jet surgical instrument is utilized, whether liquid (e.g., saline, body fluids, etc.) or air, is typically entrained by the liquid jet of the surgical instrument and can flow over the surface of the treated tissue, thereby removing debris and/or tissue macerated by the liquid jet cutting beam. In order to collect and remove debris and/or cut tissue from the operative site, as explained in more detail below, certain embodiments of the surgical instruments provided by the invention provide an evacuation lumen having a jet-receiving opening positioned opposite the jet opening of the liquid jet-forming nozzle. In such embodiments, the evacuation lumen can be configured and positioned to enable removal of the liquid comprising the liquid jet as well as, in certain embodiments, entrained liquid and/or debris. In certain embodiments of instruments providing an evacuation lumen, the instrument is configured so that the momentum generated by the liquid jet is sufficient to remove jet fluid and/or entrained fluids and debris from the operative site without requiring a source of external vacuum in fluid communication with the evacuation lumen.

As explained in more detail below, in certain embodiments of the present invention, the liquid jet surgical instruments can include a channel positioned adjacent to and downstream of a nozzle of the instrument such that at least a portion of the liquid jet passes within the channel and/or adjacent to and along the length of at least a portion of a tissue-facing opening of the channel, when the instrument is in operation. As explained below, the provision of such channel(s) in certain embodiments of the inventive instruments can provide and/or enhance at least one of, and in some embodiments many or all of, the beneficial functionalities discussed above and in more detail below.

Specifically, in one embodiment, by selectively positioning the nozzle of the instrument such that the liquid jet formed by the nozzle is located at a selected distance from a tissue-contacting surface of the channel, a particular, desired depth of cutting or ablation of tissue to be treated by the surgical instrument can be effected. In certain embodiments, the nozzle can be positioned such that the liquid jet is directed within the interior of the channel so that the surgical instrument is useful for performing lavage, wound cleaning, and/or debridement of tissue without substantial cutting or ablation of healthy tissue. As further explained below, in addition to the relative position of the nozzle and liquid jet with respect to the tissue-contacting portion of the channel of such surgical instruments, in some embodiments, further control of the cutting/washing action of the liquid jet can be obtained by varying other operating parameters, such as the pressure of the liquid forming the liquid jet, the size and shape of the liquid jet nozzle, the configuration of the above-mentioned channel, etc.

The present inventors have discovered, in the context of the present invention, that certain additional functionalities of a liquid jet surgical instrument can be provided and certain operating properties of a liquid jet surgical instrument can be made, in certain instances, more readily controllable by providing liquid jet surgical instruments with components and/or structures enabling control of the location of the liquid jet beam with respect to the surface of the tissue to be treated and/or the surface of a tissue-contacting portion of the surgical instrument and/or by providing components and/or structures enabling the degree of dispersion of the liquid jet beam and/or the interaction of the jet beam with the surrounding environment to be reduced.

In some embodiments, the liquid jet instruments provided according to the invention can include a channel at least partially surrounding and/or adjacent to at least a portion of the jet beam, which channels can include tissue-contacting portions comprising opening(s) therein of particular sizes and shapes. The sizes and/or shapes of such openings, in some embodiments, can be specifically configured to affect certain performance parameters such as the degree and extent of cutting of the tissue by the instrument, the size and shape of the tissue treatment zone, the degree of suction created by the instrument between the tissue-contacting surface and the tissue, etc. In some embodiments, the instruments provided according to the invention provide new and useful functionalities, such as those described above, and, in particular, in certain embodiments the instruments can be made easier for an operator to control and/or can be made to be more precise with regard to the depth and area of tissue removed by the instrument, and/or can be configured to selectively allow for tissue cutting, washing, or both. In some embodiments, the instruments can be further configured to allow for reproducible variation of one or more of the above-described parameters by a user of the instrument during use, and in certain particular embodiments, intraoperatively.

As mentioned above, and as described in greater detail below in the Detailed Description of the Invention, in some aspects, the invention provides a series of surgical instruments including a channel that is positioned adjacent to and downstream of the nozzle of the surgical instrument. The nozzle and channel are typically located at or near a distal end of the surgical instrument that is adapted to perform a surgical or medical procedure on a patient. Certain embodiments of the channels provided according to the invention include a longitudinally-oriented opening therein (i.e., an opening aligned or approximately aligned with the longitudinal axis of the channel), the edge(s) or surrounding surface(s) of which opening, in certain embodiments, can comprise a tissue-contacting surface(s) of the channel which can be brought into contact with tissue to be operated on by the liquid jet of the instrument. In such configurations, the tissue-contacting surface(s) of the channel typically rests on tissue adjacent to that being operated on by the jet beam. As explained in more detail below, this can, in certain embodiments, allow for control of the position of the liquid jet beam with respect to the tissue-contacting surface of the channel. Such control can enable, in certain embodiments, more precise control of the cutting depth and/or degree of cutting of the tissue with the liquid jet by the surgical instrument. In certain embodiments, additional control of the degree or extent of cutting and/or the area of operation can be effected by controlling the cross-sectional shape of the channel, the width of the longitudinally-oriented tissue-contacting opening of the channel, the angle of the jet beam with respect to the channel, etc., as explained in more detail below.

The above-mentioned, and below-described advantages and functionalities of the utilization of a channel positioned adjacent to and downstream of the jet-forming nozzle of the inventive surgical instruments can be realized, and is applicable to, both instruments designed for use in a surrounding liquid environment and instruments designed for use in a surrounding gaseous environment. However, since certain of the effects, especially the reduction of jet dispersion and the reduction of jet beam interaction with the surrounding atmosphere, can, in some instances, be more pronounced for instruments utilized in a surrounding gaseous environment, in the discussion below, such instruments and applications are highlighted. It should be understood, however, that, unless otherwise specified, the parameters, configurations, instruments, etc., discussed below could, potentially, be utilized in surgical or medical procedures in which the liquid jet beam is formed in a surrounding liquid environment as well as in a surrounding gaseous environment.

In one aspect of the invention, a surgical instrument is disclosed. In one embodiment, the instrument comprises a distal end adapted to perform a surgical procedure on a patient and a proximal end; a pressure lumen configured and positioned to conduct a liquid from the proximal end towards the distal end of the instrument; a nozzle in fluid communication with the pressure lumen that is shaped to form a liquid jet as the liquid flows therethrough; and an elongated channel, having a depth and a length, the length being measured along a longitudinal axis of the channel, the channel including a longitudinally-oriented opening to a surrounding environment extending along at least a portion of the length of the channel, the longitudinally-oriented opening having a total effective length, as measured along the length of the channel, and a width, as measured in a direction perpendicular to the longitudinal axis of the channel, wherein, the channel is positioned adjacent to and downstream of the nozzle such that at least a portion of the liquid jet passes at least one of within the channel and adjacent to and along the length of at least a portion of the longitudinally-oriented opening of the channel, when the instrument is in operation, and wherein the total effective length of the longitudinally-oriented opening exceeds the maximum width of the longitudinally-oriented opening by at least about a factor of four.

In another embodiment, a surgical instrument is disclosed, comprising a distal end adapted to perform a surgical procedure on a patient and a proximal end; a pressure lumen configured and positioned to conduct a liquid from the proximal end towards the distal end of the instrument; a nozzle in fluid communication with the pressure lumen that is shaped to form a liquid jet as the liquid flows therethrough; and a channel, having a depth and a length, the length being defined along a longitudinal axis of the channel, the channel including a longitudinally-oriented opening to a surrounding environment extending along at least a portion of the length of the channel, wherein the channel is positioned adjacent to and downstream of the nozzle such that at least a portion of the liquid jet passes adjacent to, externally of, and along a length of at least a portion of the longitudinally-oriented opening of the channel, when the instrument is in operation.

In yet another embodiment, a surgical instrument is disclosed, comprising a distal end adapted to perform a surgical procedure on a patient and a proximal end; a pressure lumen configured and positioned to conduct a liquid from the proximal end towards the distal end of the instrument; a nozzle in fluid communication with the pressure lumen that is shaped to form a liquid jet as the liquid flows therethrough; and a channel, having a depth and an length, the length being defined along a longitudinal axis of the channel, the channel including a tissue-contacting portion including a longitudinally-oriented opening to a surrounding environment extending along at least a portion of the length of the channel, wherein the channel includes at least one vent aperture configured and positioned to provide fluid communication between an interior region of the channel and the surrounding environment when the longitudinally-oriented opening of the tissue-contacting portion of the channel is occluded, and wherein the channel is positioned adjacent to and downstream of the nozzle such that at least a portion of the liquid jet passes at least one of within the channel and adjacent to and along a length of at least a portion of the longitudinally-oriented opening of the channel, when the instrument is in operation.

In yet another embodiment, a surgical instrument is disclosed, comprising a distal end adapted to perform a surgical procedure on a patient and a proximal end; a pressure lumen configured and positioned to conduct a liquid from the proximal end towards the distal end of the instrument; a nozzle in fluid communication with the pressure lumen that is shaped to form a liquid jet as the liquid flows therethrough; and a channel, having a depth and a length, the length being defined along a longitudinal axis of the channel, the channel including a longitudinally-oriented opening to a surrounding environment extending along at least a portion of the length of the channel, wherein at least one of the shape, position relative the nozzle, and dimensions of the channel is selected so that the liquid jet formed by the nozzle undergoes less dispersion along its length, when the instrument is in operation, than would a liquid jet formed by an identical instrument, not including the channel.

In another aspect, the invention involves a series of methods. In one embodiment, a method of constructing a liquid jet surgical instrument for treating a tissue of a patient with a liquid stream is disclosed. The method comprises providing a channel adjacent and downstream of a liquid jet-forming nozzle of the instrument, the channel having a length measured along a longitudinal axis of the channel, the channel including a tissue-contacting portion with a longitudinally-oriented opening to a surrounding environment extending along at least a portion of the length of the channel, wherein a shortest distance between the longitudinally-oriented opening and the bottommost inner surface of the channel defines a depth of the channel; and positioning the nozzle at a location resulting in a selected separation distance between a centerline of the nozzle and at least one of the bottommost inner surface of the channel and the tissue-contacting portion of the channel so as to achieve a desired depth of cutting and/or ablation of the tissue with the liquid emitted from the nozzle, when the instrument is in operation.

In another embodiment, a method for decreasing dispersion of a liquid jet of a liquid jet surgical instrument is disclosed. The method comprises providing a channel adjacent and downstream of a liquid jet-forming nozzle of the instrument, the channel having a length measured along a longitudinal axis of the channel, the channel including a tissue-contacting portion with a longitudinally-oriented opening to a surrounding environment extending along at least a portion of the length of the channel; and positioning the nozzle to direct a liquid jet such that it passes at least one of within the channel and adjacent to and along the length of at least a portion of the longitudinally-oriented opening of the channel.

Other advantages, novel features, and uses of the invention will become more apparent from the following detailed description of non-limiting embodiments of the invention when considered in conjunction with the accompanying drawings, which are schematic and which are not intended to be drawn to scale. In the figures, each identical, or substantially similar component that is illustrated in various figures is typically represented by a single numeral or notation. For purposes of clarity, not every component is labeled in every figure, nor is every component of each embodiment of the invention shown where illustration is not necessary to allow those of ordinary skill in the art to understand the invention. In cases where the present specification and a document incorporated by reference include conflicting disclosure, the present specification shall control.

BRIEF DESCRIPTION OF THE DRAWINGS

FIG. 6A is a schematic perspective view of an embodiment of a jet tip of a surgical liquid jet instrument having an adjustable channel shape according to one embodiment of the invention;

FIG. 6B is a schematic, partially cut-away perspective view of the embodiment of FIG. 6A;

FIG. 6C is an end view of the distal end of the embodiment of FIG. 6A;

FIG. 6D is a schematic, exploded perspective view of the embodiment of FIG. 6A;

FIG. 7A is a schematic perspective view of an embodiment of a surgical liquid jet handpiece according to one embodiment of the invention;

FIG. 7B is a schematic, fragmentary, perspective view of the internal plumbing configuration of the handpiece of FIG. 7A;

FIG. 9A is a transverse cross-sectional view of a channel-providing component of a jet tip according to one embodiment of the invention;

FIG. 9B is a transverse cross-sectional view of a channel-providing component of a jet tip according to another embodiment of the invention;

FIG. 9C is a transverse cross-sectional view of a channel-providing component of a jet tip according to another embodiment of the invention;

FIG. 9D is a transverse cross-sectional view of a channel-providing component of a jet tip according to another embodiment of the invention;

FIG. 9E is a transverse cross-sectional view of a channel-providing component of a jet tip according to another embodiment of the invention;

FIG. 10A is a schematic perspective view of a jet tip of a surgical liquid jet instrument according to one embodiment of the invention;

FIG. 10B is a longitudinal cross-sectional view of a jet tip having a flared distal end according to another embodiment of the invention;

FIG. 12A is a schematic top perspective view of a jet tip of a surgical liquid jet instrument according to one embodiment of the invention;

FIG. 12B is a schematic top perspective view of the jet tip of FIG. 12A;

FIG. 12C is a top plan view of the jet tip of FIG. 12A; and

FIG. 12D is a longitudinal cross-sectional view of the jet tip of FIG. 12C taken along lines 12D-12D.

DETAILED DESCRIPTION

Figure 1:
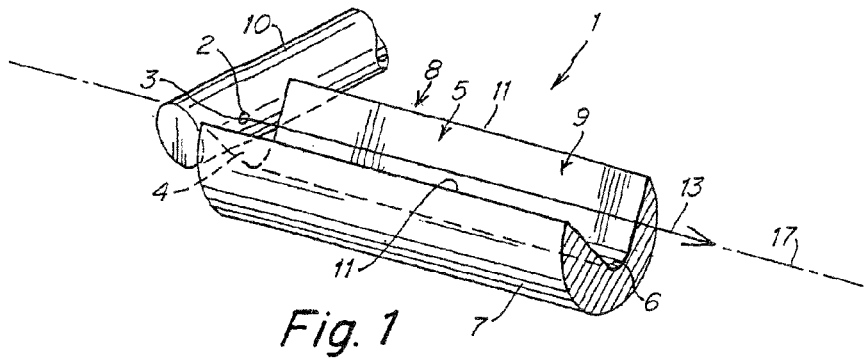
FIG. 1 is a schematic perspective view of a jet tip of a surgical liquid jet instrument according to one embodiment of the invention.

The surgical instruments provided according to certain embodiments of the invention can take on many configurations, depending on the particular application. For example, the surgical instruments can comprise a surgical handpiece with a body designed to be gripped by the hand of an operator during a surgical or medical procedure. Alternatively, the surgical instruments can comprise an elongated tubular device, such as a catheter, or can take on other configurations. Additional configurations which can embody certain aspects of the present invention are discussed in Applicants' U.S. Pat. No. 6,375,635. Such instruments typically include a "distal end" and a "proximal end." A "distal end" of a surgical instrument, according to the invention, refers to that portion of the instrument that is adapted to perform a surgical procedure on a patient. The distal end typically includes such structure as the jet nozzle, jet-interacting channel, and other tissue-contacting and/or tissue-altering components. While the "distal end" is typically located at a position on the instrument farthest from the operator during use (i.e., a distal-most position), this need not always be the case. The "proximal end" of the instrument refers to that portion of the instrument adapted to be controllable by an operator of the instrument. For embodiments wherein the instrument comprises a surgical handpiece, the proximal end typically includes a body configured and adapted to be grasped by the hand of an operator during use. While, in the discussion below, the surgical instruments are typically referred to as being "liquid jet" instruments, it should be understood that, while, in certain embodiments involving tissue cutting, the use of liquids to form the liquid jet is preferred, in alternative embodiments, surgical instruments according to the invention could utilize fluids other than liquids, such as certain gases. Accordingly, wherever "liquid" or "liquid jet" is indicated, the terms "fluid" (encompassing both liquids and gases) and "fluid jet," respectively, should also be inferred as being equivalent, unless otherwise specified.

The term "jet tip," as used herein, refers to an assembly of components at the distal end of the instrument with which the liquid jet is created and manipulated and, optionally, evacuated from the site of treatment. Accordingly, the "jet tip" typically includes the liquid jet nozzle portion of the high pressure lumen of the instrument, the jet-interacting channel structure of the instrument, and, for embodiments including evacuation, the jet-receiving opening and the distal end of the evacuation lumen as well as any connecting sleeve present connecting the channel to the more proximal portions of the evacuation lumen.

A "jet-interacting channel" or, equivalently, "channel," as used herein, refers to a novel structure provided according to certain embodiments of the present invention that is positioned adjacent to and downstream of the nozzle of the instrument such that, during operation and when the liquid jet is not impinging upon tissue or other material within the site of operation, at least a portion of the liquid jet passes within the channel and/or adjacent to and along the length of at least a portion of a longitudinally-oriented opening of the channel. "Channel," geometrically, refers to a conduit having at least one opening longitudinally directed along at least a portion of the length of the conduit (i.e., the "longitudinally-oriented opening"), which opening is located and positioned within the instrument, as described and shown in more detail below, to be, at least approximately, aligned with the longitudinal trajectory of the liquid jet, when the instrument is in operation and the liquid jet is not impinging tissue or other material in the operative site; the longitudinally-oriented opening is also positioned such that it is facing and able to be brought into contact with tissue within an operative site to be cut, ablated, or otherwise manipulated by the jet tip. In addition to the longitudinally-oriented opening included in the tissue-contacting portion of the jet-interacting channel of the instrument, such channels, in certain embodiments, can also be open at their distal and/or proximal ends, providing a fluid inlet and outlet, respectively. Such embodiments can enable, as described below, a jet beam produced by the instrument to be directed within and through a channel during operation. While the term "channel," as used in the above context, is often used to refer to the geometric void space defining the fluid flow area and the surrounding walls defining the void space, this term is also used herein to refer to the physical structure and/or component (such as an insert, or other portion of the distal end of the instrument) providing the void space and/or in which such void structure is formed. Unless otherwise noted, the terms "channel" and "jet-interacting channel," can be used, herein, interchangeably and have the same meaning.

As discussed and illustrated in more detail below, certain jet-interacting channels utilized in some embodiments of the invention include at least one "ventilation aperture" therein.

The term "ventilation aperture" or "vent aperture," as used herein, refers to an opening of the channel that is configured and positioned to provide fluid communication between an interior region of the channel and the environment surrounding the jet tip when the longitudinally-oriented opening of the tissue-contacting portion of the channel is occluded. In other words, such vent apertures can provide the ability to decrease the level of suction created within the interior region of the channel during operation, even under conditions where the tissue completely occludes the tissue-contacting, longitudinally-oriented opening of the channel. This can permit, as discussed below, the instruments to glide over tissue more easily and with less perceived "stickiness," as well as allowing, in some instances, more precise control over the level of cutting and/or evacuation with the instrument. Vent apertures, as discussed and illustrated below, can comprise an open inlet area of the channel (i.e., a cross-sectional area at the upstream end of the channel adjacent the nozzle that is not blocked by the liquid jet-emitting nozzle or distal end of the high pressure lumen). In these, or in alternative, embodiments, vent apertures can also be configured as holes, slits, or otherwise configured openings located anywhere along the length of the channel. In a particular embodiment, as shown and discussed below, the vent apertures can comprise ridges, grooves, indentations, etc., created in a tissue-contacting surface of the tissue-contacting portion of the channel. As discussed in more detail below, in general, an increase in the total cross-sectional area of the vent apertures provided in the channel tends to diminish the level of suction created within the interior region of the channel during operation. The amount of venting, in some embodiments, can be controlled by an operator, (in some embodiments intraoperatively), by varying the open area of the vent aperture(s). In some embodiments, the vent aperture can be configured to open and close automatically, depending on the level of suction present within the interior region of the channel during operation.

The term "beam height" or "jet beam height" refers to a shortest distance existing between the location of a center line defining the central region of the jet beam formed by the nozzle, at a given point along the length of jet beam travel, and a plane tangent to the tissue-contacting surfaces defining the opposed sides of the longitudinally-oriented opening of the channel (i.e. a plane co-planar with the plane defining the longitudinally-oriented opening of the channel). Stated another way, the beam height can also be defined as the perpendicular distance between a center line defining the central region of the jet beam and the plane defining the longitudinally-oriented opening, as measured in a plane that is transverse to the longitudinal axis of the channel and that is perpendicular to the plane defining the longitudinally-oriented opening. It should be noted that this height can, in some embodiments, vary along the length of the jet beam (e.g., for embodiments wherein the jet beam is directed at an up or down angle with respect to the longitudinal axis of the channel—i.e., at an angle with respect to the longitudinal axis within a plane perpendicular to both the plane defining longitudinally-oriented opening and a plane that is transverse to the longitudinal axis of the channel. Beam heights have positive values when the center line of the jet beam is located external to the interior region of the channel and have negative values when the centerline of the jet beam is located within the channel. A beam height of zero indicates that the location of the centerline of the jet beam is within the plane defining longitudinally-oriented opening of the channel (i.e. the plane tangent to the tissue-contacting surfaces defining the opposed sides of the longitudinally-oriented opening of the channel). Also, where reference is made herein to "medical" or "surgical" uses, it is intended that either of these terms encompass the other as well as use in a veterinary or cosmetic application, unless otherwise specified.

It has been discovered within the context of the present invention that by provision of a jet-interacting channel in a liquid jet surgical instrument, certain operational characteristics of the instrument can be improved for certain applications. While the provision of a liquid jet-interacting channel in the jet tip of a liquid jet surgical instrument can potentially provide beneficial performance for a wide variety of interests and a wide variety of surgical and medical applications, the jet-interacting channel has been found to be especially useful for instruments configured to direct a liquid jet tangentially or parallel to the surface of a tissue to be treated for applications involving the cutting or removal of a desired depth or amount of tissue (e.g., in a fashion similar to "slicing" or "planing") and/or to applications involving washing and lavage of tissue (e.g., at a wound site). While the inventive devices, structures and methods described herein can, in certain cases, be used for instruments intended to be operated while submerged in a liquid surgical environment, the instruments have particular utility for instruments designed for use in a surrounding air or gaseous environment.

Without being tied to a particular physical or fluid-mechanical theory or explanation of the function of the jet-interacting channels provided according to the invention, it is believed that such channels, as configured and provided according to the invention, can interact with the jet beam created by an instrument in such a way that they can reduce the degree of dispersion of the jet beam along its length, when compared to a substantially identical liquid jet instrument but not including the jet-interacting channel. It is also believed that the jet-interacting channels provided according to the invention may achieve their beneficial function, at least in part, by reducing the level of interaction between the liquid comprising the jet beam and the air or liquid environment surrounding the jet tip, in which the jet beam is formed. Specifically, it is believed that by directing the jet beam within the channel or closely adjacent to and along a longitudinally-oriented opening of the channel, that the channel can serve to reduce the size of the entrainment region surrounding the jet beam and can focus the entrainment region on only one side of the jet beam, thus decreasing the degree of dispersion of the jet beam along its length. Specifically, it is believed that the provision of the jet-interacting channels provided according to certain aspects of the invention can enable the instruments to provide an extended cutting length of the jet beam for a given nozzle configuration, when compared to an instrument not including such channel, due to, it is believed, at least in part, the jet-interacting channel's ability to reduce the breakup of the jet (e.g., into droplets), which tends to result in higher levels of dispersion. In addition, as discussed and illustrated below, the longitudinally-oriented opening of the channel can also define an area of interaction of the jet beam with the tissue to be treated, thereby allowing for the area, shape, depth, etc., of the region of the tissue to be treated to be varied according to the geometry and size of the longitudinally-oriented opening of the channel. Such control can be advantageous when utilizing the inventive instruments for specific medical or surgical procedures.

It has also been discovered, within the context of the invention, that by selective variation of certain physical and geometric properties of the jet tip, and especially the jet-interacting channel portion of the jet tip, that it is possible to adjust and control, in an advantageous fashion, some or many of the functional/performance characteristics of the surgical liquid jet instruments provided according to the invention. In certain embodiments, described in more detail below, some such parameters, for example the beam height of the jet with respect to the channel, the cross-sectional shape of the channel and/or the width of the longitudinally-oriented opening of the channel, etc., can be varied by an operator of the instrument, optionally intraoperatively, so as to enable fine tuning of the operational and functional characteristics of the instrument during a surgical procedure. Control of certain geometric characteristics of the jet tip, optionally in conjunction with control of the liquid pressure supplied to the nozzle for forming the liquid jet, can allow, as discussed in more detail below, the construction of liquid jet surgical devices, according to the invention, having certain predictable and advantageous properties.

FIG. 1 illustrates a first embodiment of a jet tip 1 provided at the distal end of a surgical instrument according to one embodiment of the invention. A pressure lumen 10 is provided that is configured and positioned to conduct a liquid from the proximal end of the instrument (not shown) towards the distal end of the instrument. In the embodiment illustrated, the distal end of pressure lumen 10 is sealed and a nozzle 2 is formed in the sidewall of the lumen by, for example, drilling or etching. It should be noted that the illustrated configuration of the distal end of high pressure lumen 10 and the nozzle 2 is merely exemplary and that a wide variety of other techniques for forming the nozzle can be utilized. A number of such techniques, and exemplary nozzles formed thereby, which can be used in certain embodiments of the present invention, are described in detail in Applicants' U.S. Pat. No. 6,375,635.

In general, the nozzle can be formed in the high pressure lumen by any means known to those of ordinary skill in the art. The diameter and shape of the jet opening 3 of the nozzle 2 is selected and determined based on the desired cross-sectional diameter of the liquid jet beam formed by the instrument and can vary depending on the particular applications and uses of the instrument. In certain typical embodiments involving instruments designed for liquid jet cutting and/or lavage, the diameter of the jet opening of the nozzle can vary within a range from about 0.001 inch to about 0.01 inch. In one particular and exemplary embodiment, the diameter of jet opening 3 of nozzle 2 is about 0.005 inch.

As discussed in Applicant's U.S. Pat. No. 6,375,635, another consideration when forming the nozzle concerns the ratio of the minimum diameter of the nozzle, as described above, to the total length of the nozzle having such minimum diameter (the "nozzle length" or "characteristic length of the nozzle") (i.e., as measured along the center line of the nozzle). In general, the greater the ratio of this characteristic length of the nozzle to the minimum diameter of the nozzle the greater the degree of coherence of the jet beam formed by the nozzle and the lesser the degree of dispersion of the jet beam with distance from the jet opening of the nozzle, but also the greater the pressure drop across the nozzle. For many embodiments, it is desirable that the jet beam be relatively coherent over its cutting length (described below). It has been found, in the context of the present invention, that the provision of a jet-interacting channel (e.g., channel 9, described in more detail below) can increase the level of coherence of the jet beam and reduce dispersion along its length. Accordingly, in certain embodiments of the present invention, a smaller ratio of characteristic nozzle length to minimum nozzle diameter can be employed to achieve a similar degree of coherence for a liquid jet emitted from a nozzle, when compared to typical prior art liquid jet surgical instruments not including a jet-interacting channel. This can allow the present instruments including such channels to operate, in some instances, with somewhat reduced liquid jet-forming liquid pressures and/or allow the ability to use shorter nozzles to achieve a particular degree of jet coherence with the instrument. Typically, nozzles provided in the instruments according to the invention can have a characteristic nozzle length to minimum jet opening diameter ratio of from between about 1:1 to about 10:1. In one exemplary embodiment, the nozzle has a characteristic nozzle length to minimum jet opening diameter ratio of about 4:1.

As discussed in detail in Applicants' U.S. Pat. No. 6,375,635, the particular liquid pressure of the liquid supplied to the nozzle for forming the liquid jet depends upon the particular application for which the surgical instrument is to be used. Specifically, the pressure of the liquid forming the liquid jet affects the momentum of the liquid jet and the cutting power of the liquid jet. In general, the higher the liquid pressure, for a given nozzle configuration, the greater the cutting and ablation power of the liquid jet formed thereby. For typical embodiments of the present invention for forming a liquid jet for cutting and/or ablating tissue, the liquid pressure supplied to the nozzle of the instrument will typically vary within a range of between about 1000 psig to about 20,000 psig, with a range of between about 1000 psig and about 6000 psig typically employed for creating liquid jets able to cut softer tissue while not substantially cutting more tenacious tissue, such as bone, cartilage, nerve tissue, etc. For embodiments wherein the surgical instruments provided according to the invention are designed primarily for debridement, washing, and/or lavage, lower pressures than those mentioned above may be advantageously utilized.

In some embodiments, as illustrated, the nozzles of the inventive instruments can comprises a small diameter hole etched into the side of the high pressure tube. Such holes can be conveniently formed by techniques known in the prior art such as those including, but not limited to, electrochemical etching (e.g. "EDM" in which a thin electrode is positioned at the site of the nozzle and an electrical potential is applied to cause electricity to run from the electrode to the site thereby eroding a hole at the site), laser etching, micro-sandblasting, or mechanical drilling. In alternative embodiments, as discussed in more detail in Applicants' U.S. Pat. No 6,375,635, the nozzle can be formed by drawing down the distal end of the high pressure lumen to the desired nozzle diameter and, in some embodiments if necessary or desired, bending and/or offsetting the necked down region of the lumen to enable the liquid jet to be directed along the longitudinal axis of the channel of the instrument. In yet other embodiments, the nozzle could be separately fabricated and subsequently connected to the tubing. In one particular embodiment, the nozzle is formed within a cylindrical insert which is inserted in a larger diameter hole in the sidewall of the high pressure lumen by and secured by an appropriate technique including, for example, press fitting and/or brazing.

Returning to FIG. 1, nozzle 2 is positioned upstream and adjacent to, and in some embodiments apposed against, inlet face 4 of channel 9. Jet-interacting channel 9, as illustrated, comprises a void 5 having a bottommost portion 6 formed in a channel-providing structure 7. It should be understood that the shape and configuration of structure 7 as shown (i.e. cylindrical) is not required in all embodiments. The structure forming the channel may have any shape compatible with containing a channel of the desired dimensions and shape and may, in some embodiments as discussed below, comprise a separate and, alternatively, removable element, such as an insert, or may comprise part of the permanent structure of the distal end of the surgical instrument.

A liquid jet 13 emitted by nozzle 2 is directed and positioned such that it passes within channel 9 along a direction essentially parallel to the longitudinal axis 17 of the channel. Channel 9 further includes a longitudinally-oriented opening 8 extending along the entire length of the channel, which, in operation, comprises a tissue-contacting portion of the channel that is placed against the surface of a tissue to be treated. In operation, in such embodiments, the tissue would typically make contact with the channel at tissue-contacting surfaces 11.

Various configurations of an entire jet tip for an embodiment of the invention providing the ability to evacuate liquid and debris from the surgical site are illustrated in FIGS. 2A-2D. These figures will be used to illustrate and discuss certain geometric relationships which can affect performance of the jet tip. In the embodiment 15 illustrated in FIG. 2A, high pressure lumen 10 is bent so that its distal end forms approximately a right angle with the longitudinal axis 17 of the jet tip so that the liquid jet 13 emitted by nozzle 2 passes within channel 9 and travels down the longitudinal length of the channel. The distal end of the high pressure lumen 10 does not fully occlude the inlet face 4 of channel 9 leaving an open aperture therein providing a vent aperture. While the axially-oriented jet tip configuration of jet tip 15 is illustrated as a particular example herein, it should be understood that in alternative embodiments other geometric configurations and relative orientations of the jet tip with respect to the proximal end and/or body of the surgical instrument are possible. Many suitable alternative configurations, which can also be used in the context of the present invention, are discussed and illustrated in Applicants' U.S. Pat. No. 6,375,635.

Jet beam 13 passing within and along channel 9, when the instrument is utilized in a surgical procedure, will interact with tissue apposed to longitudinally-oriented opening 8 of channel 9 and in contact with tissue-contacting surfaces 11. After passing through channel 9, jet beam 13 passes into a connecting sleeve 12, forming a distal end of the evacuation lumen 16. Connecting sleeve 12 includes at its distal end an opening 14 comprising a jet-receiving opening. Channel 9 is connected in fluid communication with the distal end of the evacuation lumen 16 via connecting sleeve 12. Connecting sleeve 12, as illustrated, is configured to hold channel 9 in place in the jet tip, optionally in cooperation with high pressure tube 10 or other restraining means at the distal end of the channel. The connection between component 7 carrying channel 9 and sleeve 12 can be made more permanent, in some embodiments, by a variety of well-known techniques, for example by gluing, brazing, welding, press fitting, or by other means known to those of ordinary skill in the art. In alternative embodiments, the connection can be non-permanent and channel-providing component 7 can comprise an insert that is removable and replaceable by an operator of the instrument. In alternative embodiments, sleeve 12 can be integrally formed with component 7 and/or evacuation lumen 16. In certain embodiments, as illustrated, sleeve 12 can be separate from and permanently or reversibly connected to evacuation lumen 16, which is configured to evacuate material from the jet tip to the proximal end of the instrument (not shown) and, typically, to a drain (not shown) through an evacuation tube of the instrument (such as evacuation tube 86 shown in FIG. 7 below).

Jet-receiving opening 14 of sleeve 12 can be configured to collect both the liquid comprising the liquid jet as well as any liquid, air, and/or tissue debris that is entrained by the liquid jet during operation of the instrument. In some embodiments, as discussed below and in more detail in Applicants' U.S. Pat. No. 6,375,635, the sleeve and/or evacuation lumen can be configured and operated so that the momentum and energy of the liquid jet can drive the entrained fluid through the evacuation lumen to the proximal end of the instrument (not shown) without the need for providing a source of external vacuum or suction in fluid communication with the evacuation lumen. In addition, also as described below and in more detail in Applicants' U.S. Pat. No. 6,375,635, the shape and size of the jet-receiving opening 14 and the evacuation conduits (e.g., sleeve 12 and evacuation lumen 16) can be selected and configured to provide certain venturi effects and/or other physical and fluid mechanical phenomena enhancing fluid and debris removal from the site, if desired.

In certain embodiments, especially those for which the surgical instrument includes jet and/or debris evacuation not requiring an external source of suction, certain size and geometric parameters of the connector 12, if present in evacuation lumen 16, or, if not present, at the distal end region of the evacuation lumen, can be provided. For example, in certain embodiments, in order to minimize backspray and resistance to evacuation flow, it is desirable that any opening in the downstream end of channel 9 be smaller in cross sectional area or essentially equal in cross sectional area to the cross sectional area of the jet-receiving opening 14 immediately adjacent to and downstream of the downstream end of the channel. In some embodiments, the downstream open end of the channel is made flush with the adjacent portion of the jet-receiving opening so that there exist no surfaces impeding fluid flow or occluding any portion of the channel which could, when the instrument is in use, cause deflection or bounce back of the fluid flowing from the channel into the evacuation lumen. While the particular size of the jet-receiving opening depends, of course, on the size and/or cross-sectional shape of the jet-interacting channel, in typical embodiments, the jet-receiving opening has a maximum cross-sectional diameter ranging between about 0.01 inch to about 0.2 inch, more typically between about 0.03 inch to about 0.1 inch and, in one particular embodiment, has a maximum cross sectional diameter of about 0.06 inch.

In some embodiments, not illustrated, the distal end of the evacuation lumen or connector, for those embodiments including a connector between the evacuation lumen and the channel, can be configured to include a constriction (i.e., a necked region of reduced diameter) downstream of the jet-receiving opening, thereby creating a venturi. In such embodiments, the diameter of the reduced diameter neck region of the venturi can be advantageously sized to be equal to or in excess of the diameter of the liquid jet measured at the plane of the entrance of the region of minimum diameter of the reduced diameter neck portion. The diameter of the liquid jet at this location typically will be, as will be readily understood by those of ordinary skill in the art, somewhat greater than the diameter of the liquid jet-forming nozzle on account of dispersion and expansion of the liquid jet along its length. This dispersion tendency can be reduced by the novel provision of the jet-interacting channel 9 as described above. In some embodiments, channel 9 can interact with jet 13 so that the diameter of the jet as it enters the jet-receiving opening does not exceed the diameter of the jet as emitted from the nozzle, for typical jet beam lengths described below, by more than a factor of about 30, in some embodiments by more than a factor of about 20, in other embodiments by more than a factor of about 10, in other embodiments by more than a factor of about 5, in other embodiments by more than a factor of about 4, in other embodiments by more than a factor of about 3, and in yet other embodiments by more than a factor of about 2. For embodiments including a venturi, as discussed above, the dispersed diameter of the liquid jet entering the reduced diameter neck portion of the constriction typically can have a diameter ranging from about 20% to about 100% of the minimum diameter of the constricted region and can have a diameter, as measured at the plane the distalmost portion of the jet-receiving opening, of between about 20% and about 50% of the maximum cross-sectional dimension of the jet-receiving opening as measured at this point.

Referring again to FIG. 2A, while connecting sleeve 12 can be made of any suitable materials, including, but not limited to, various hard plastics and metals such as those described in Applicant's U.S. Pat. No. 6,375,635, in certain embodiments, the sleeve is made of a surgically compatible metal, such as stainless steel. In general, the materials selected for forming various components of the jet tip and the surgical instruments described herein can be substantially similar to those described in Applicants' U.S. Pat. No. 6,375,635. For embodiments wherein evacuation lumen 16 is constructed of a resilient material more prone to erosion by contact with a liquid jet than are the materials from which connecting sleeve 12 is formed, it can be desirable to have connecting sleeve 12 extend proximally into evacuation lumen 16 for a distance at least sufficient to enable the liquid jet 13 to impinge upon the inner surface of connector 12, as opposed to evacuation lumen 16.

Figure 2A:
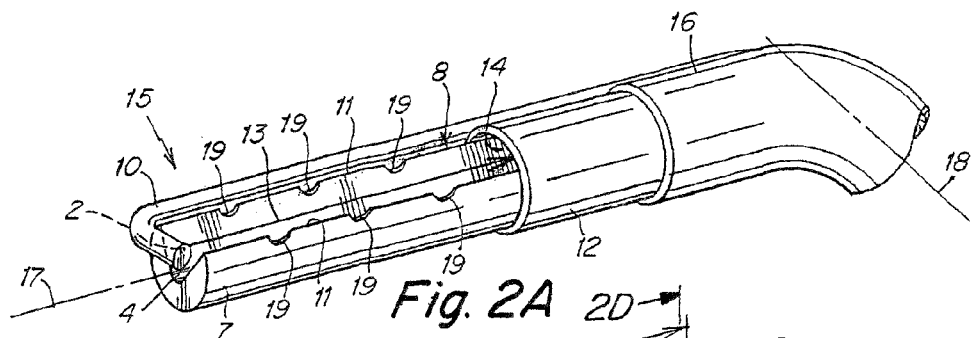
FIG. 2A is a schematic perspective view of an alternative embodiment of a jet tip of a surgical liquid jet instrument according to another embodiment of the invention.

In some embodiments, evacuation efficiency can be enhanced by providing an enlargement in the internal diameter of the connector 12 and/or evacuation lumen 16 proximally of the jet-receiving opening 14 and proximally of any constriction forming a venturi, should one be present. In certain such embodiments, the inner diameter of the sleeve and/or evacuation lumen increases from a certain minimum value at a first, distal location to a certain maximum value at a more proximal location, whereinafter, the internal diameter of the evacuation lumen remains constant. More detail concerning the configuration of the evacuation lumen in such embodiments can be found in Applicants' U.S. Pat. No. 6,375,635. In certain embodiments, wherein the liquid jet is not directed in parallel to the longitudinal axis of channel 9, as illustrated in FIG. 2A, but rather is angled downwardly into the channel, with respect to the orientation as illustrated, evacuation of fluid can be further facilitated by setting the longitudinal axis of the connecting sleeve at an angle with respect to the longitudinal axis 17 of the distal end of evacuation lumen 16 so as to match the downward angle of the jet beam emitted from the nozzle so that the longitudinal axis of the connecting sleeve is colinear with the trajectory of the jet beam. Such a configuration has relevance for embodiments including angled jet beams such as those illustrated below in FIGS. 12A-12D. Also, in certain embodiments, to facilitate the manipulation of the instrument and to enable the tissue contacting surfaces 11 of channel 9 to be apposed to a tissue to be treated with the instrument more easily, the longitudinal axis 17 of the jet tip can be set at an angle with respect to the longitudinal axis 18 of the proximal end/body (not shown) of the instrument. In certain embodiments, the angle between longitudinal axis 17 of the jet tip and longitudinal axis 18 of the proximal end (not shown) of the instrument can range from about 15 degrees to about 90 degrees to provide desirable ergonomics for an operator of the instrument.

FIG. 2A also illustrates one configuration for providing vent apertures according to one embodiment of the invention. Tissue contacting surfaces 11, as illustrated, include a plurality of indentations 19 therein. Although, in the illustrated embodiment, indentations 19 comprise semicircular indentations, it should be appreciated that in other embodiments, the particular shape and number such indentations and their locations along the length of tissue contacting surfaces 11 could be varied to achieve a desired degree of venting. Vent apertures 19 permit fluid communication between the atmosphere surrounding jet tip and the interior region of channel 9 even when a tissue being treated is brought into contact with tissue-contacting surfaces 11 such that the tissue essentially completely occludes longitudinally-oriented opening 8 of channel 9. The provision of vent apertures, such as apertures 19, can improve the tissue treating characteristics of the instrument and the ease of use of the instrument by reducing the tendency of the jet tip to "stick" to the surface of the tissue being treated during use. Appropriate venting can enable the jet tip to more readily glide over the surface of tissue during use, and can reduce the tendency of tissue to be undesirably deformed into the interior region of channel 9, when the instrument is in operation.

Figure 2B:
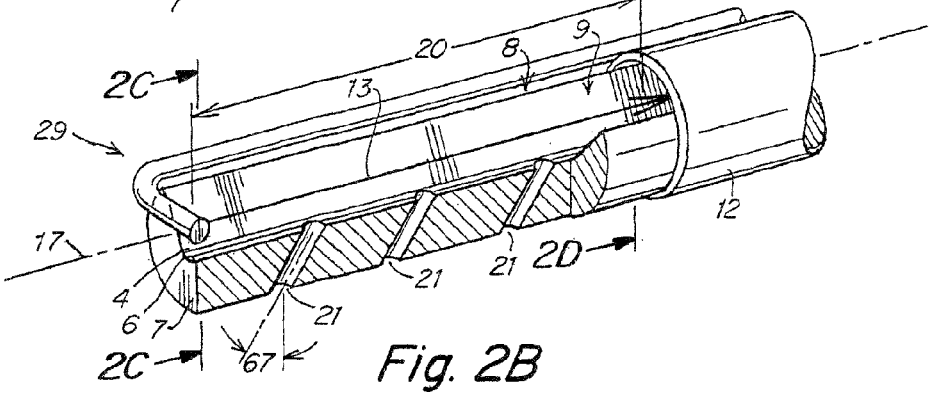
FIG. 2B is a schematic, partially cut-away perspective view of another alternative embodiment of a jet tip of a surgical liquid jet instrument according to another embodiment of the invention.

FIG. 2B illustrates, in partial cross section, a jet tip 29 having a similar configuration as that illustrated in FIG. 2A except providing differently configured venting apertures along the length of the channel 9. FIG. 2B also illustrates the definition of jet beam length 20 of jet beam 13. The jet beam length defines the effective cutting length and/or tissue-interacting length of jet beam 13, when the instrument is in use. As discussed above, the inventive provision of a jet-interacting channel 9 adjacent to and/or at least partially surrounding liquid jet 13 is believed to reduce the degree of dispersion of the liquid jet over its length enabling longer jet lengths to be achieved for a given nozzle length to nozzle diameter ratio. While, in certain embodiments, the length 20 of jet beam 13 could be essentially any length desirable, for typical configurations utilized in surgical instruments, the jet length will range from about 2 millimeters to about 3 centimeters and, more typically, will fall within a range of from about 1 centimeter to about 2 centimeters. As discussed below in the context of FIGS. 2C and 2D, the maximum channel width and/or the maximum width of the longitudinally-oriented opening 8 of the channel can also be a function of the desired length of the liquid jet and/or longitudinally-oriented opening of the channel.

In the embodiment illustrated in FIG. 2B, jet length 20 is essentially equal to the effective length of channel 9 of the jet tip. In the illustrated embodiment, longitudinally-oriented opening 8 extends along the entirety of the length of channel 9. However, in other embodiments, the longitudinally-oriented opening 8 may extend over only a part of the total beam length 20 of jet beam 13 such that the total effective length of the longitudinally-oriented opening is less than the beam length 20 of jet beam 13. The "total effective length" of the longitudinally-oriented opening, as used herein in the above context, refers to the cumulative length of all segments (for embodiments where the channel has multiple segments) of the longitudinally-oriented opening (as measured along the length of the channel), which can interact with and affect at least one property of the liquid jet. In certain embodiments, other than those illustrated, the channel, instead of being a single piece which is continuous along its length, could be comprised of a plurality of shorter channel segments sequentially and longitudinally stacked, with respect to each other, along the flow path of the jet beam, optionally, with spaces in between segments that could provide vent apertures. In such an embodiment, the "effective length" of the tissue-facing openings collectively comprising the "longitudinally-oriented opening" would be equal to the sum of the lengths (as measured along the longitudinal axis of the jet tip) of the tissue-facing openings of the individual segments. In the discussion below, and in the claims, where certain ratios of channel width, width of the longitudinally-oriented opening, or other parameters are specified with respect to the "effective length" of the longitudinally-oriented opening of the channel, such parameters are determined with reference to the above-described effective length, namely the cumulative length, as measured along the length of the channel, of all of the individual segments openings comprising the overall channel opening of the device.

FIG. 2B also illustrates an alternative for providing vent apertures along the length of channel 9. Channel 9 includes vent apertures 21 formed in bottommost surface 6 of the channel. These vent apertures can provide controlled relief of the vacuum tending to be formed in the interior region of channel 9, which can tend to press the jet tip against the tissue, as is further discussed below. Vent holes 21 can be drilled or otherwise formed at a particular angle 22 measured in a plane normal to the longitudinal axis 17 of channel 9. In certain embodiments, angle 22 is greater than 0 (i.e., vent holes 21 slant distally from bottommost surface 6 of channel 9 to the outer surface of component 7). Such a slant can prevent inadvertent entry of part of jet beam 13 into one or more of the vent holes during operation. Typically, angle 22 would range from between about 45 degrees to about 60 degrees. In alternative embodiments, instead of locating vent holes 21 such that they are in fluid communication with bottom surface 6 of channel 9, vent holes could be placed in fluid communication with one or both of the side surfaces of channel 9.

Figure 2C:
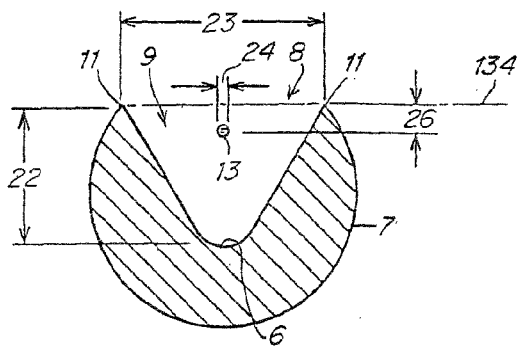
FIG. 2C is a transverse cross-sectional view of the embodiment of FIG. 2B taken along lines 2C-2C.
Figure 2D:
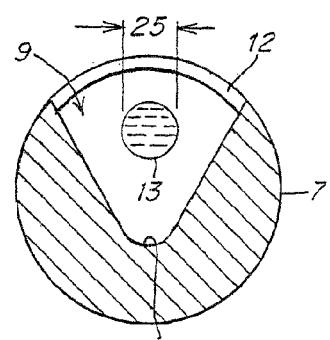
FIG. 2D is a transverse cross-sectional view of the embodiment of FIG. 2B taken along lines 2D-2D.

Reference is now made to FIGS. 2C and 2D illustrating jet-interacting channel 9 as it appears in cross section in a plane perpendicular to its longitudinal axis. These views will be used to illustrate certain geometric parameters of the channel that can affect its performance in the inventive surgical instruments. Such parameters include the cross-sectional shape of the channel, the depth 22 of the channel, the volume of the open area of the channel, the width 23 of the channel and/or longitudinally-oriented opening 8 of the channel in relationship to the length 20 of the jet beam and/or the length of the channel and/or the longitudinally-oriented opening, the initial unexpanded diameter 24 of jet beam 13, the maximum diameter 25 of the expanded jet beam at the end of its length of travel, and the beam height 26 of the center line of the jet beam with respect to the plane 134 defining the longitudinally-oriented opening 8 of the channel. As explained below, at least one of, and commonly several or each of the above-recited geometric parameters can be important in defining the functional characteristics and the performance of the jet tip of the surgical instrument. While certain general guidelines and considerations are discussed below directed to selecting such parameters, as would be apparent to those of ordinary skill in the art, the particular dimensions and parameters must be selected, with guidance from the teachings herein, based on the particular application and desired characteristics of instrument under consideration utilizing routine experimentation and optimization.

The cross-sectional shape of the channel, which for channel 9 of the illustrated embodiment, comprises a "V" shape with a rounded bottom, can take on a wide variety of forms, depending on the needs of a particular application. In general, the cross-sectional shape can affect the hydrodynamic characteristics of the jet tip and the cutting and/or lavage characteristics of the jet beam-induced fluid flow. While the precise effect of any particular shape on the hydrodynamic characteristics of the jet tip is difficult to predict precisely, in general, it is believed that more open geometries, such as the open "C" configuration illustrated below in FIGS. 9 and 11 and configurations, such as the "V" shown, having a relatively wide channel width as a function of channel volume, generally yield jet tips creating a relatively high level of fluid aspiration and entrainment for a given jet beam velocity, which tips can be suitable or advantageous for instruments utilizing jet beams for lavage or debridement (e.g. without substantial tissue cutting), especially when used in conjunction with negative beam heights, such as illustrated in FIGS. 2C and 2D.

As discussed above, the width and area of the longitudinally-oriented opening of the channel defines an area of action of the jet on the tissue apposed to the longitudinally-oriented opening of the channel so that wider channels will tend to operate over a larger area of tissue than narrower channels. Wider channels, as discussed above, often create higher levels of tissue aspiration into the channel and, accordingly, can often result in greater degree of lifting of the tissue into the channel during operation, which can, in turn, result in, for a given beam height, a deeper level of cut or more aggressive treatment of the tissue, and which can lead to more variability of cutting and/or ablation depth along the length and across the width of the longitudinally-oriented opening. Accordingly, for applications where more controllable depths of tissue cutting with the jet beam is desirable (e.g., for embodiments such as certain embodiments discussed below, wherein the jet beam height is positive and the instrument is used for "slicing" or "planing" tissue layers from a surface), it may be advantageous to provide a channel having a cross-sectional shape that is relatively narrow and shallow or narrow and deep. For example, in some embodiments, the channel could have a cross-sectional shape that is "U" shaped, rectangular, or square. In some such embodiments, it is advantageous to select a shape providing a channel having an interior region with a maximum width that is essentially equal to the maximum width of the longitudinally-oriented opening of the channel (i.e., width 23).

In certain embodiments, especially those wherein the instrument is used for liquid jet cutting/ablation applications, it can be desirable to configure the channel so that the maximum width 23 of the longitudinally-oriented opening of the channel (e.g., opening 8 of channel 9), and/or the maximum width of the interior region of the channel is large enough to prevent undesirable contact of expanded jet beam diameter 25 with the walls of the channel, when the instrument is in operation under conditions where the jet beam is not striking tissue or other objects in the surgical field. In certain embodiments, it is desirable to configure the channel so that the maximum width of the channel and/or the longitudinally-oriented opening at the downstream end of the channel is as small as feasible, while preventing contact between the expanded jet beam and the walls of the channel. For similar reasons, it can be generally advantageous to align the jet beam with respect to the longitudinal axis of the channel such that the jet beam is generally parallel to the longitudinal axis (as measured in the horizontal plane with respect to the orientation shown in FIGS. 2C and 2D—e.g. plane 134 as shown), or, alternatively, is directed at a small enough angle with respect to the longitudinal axis such that the expanded beam does not contact the walls of the channel over its travel length 20.

In general, the particular width of the channel and/or the width of the longitudinally-oriented opening of the channel with respect to the diameter of the nozzle, the length of the nozzle, the cutting length of the jet beam, the effective length of the longitudinally-oriented opening of the channel, the liquid pressure supplied to form the jet beam, etc., should be selected based upon routine experimentation and optimization for a particular configuration and use. In general, screening tests to determine such relationships and design criteria for selecting such parameters can be based upon following general methodology. First, for a given surgical or medical application, a desired cutting or treatment length of the jet beam can be specified. Next, for a particular selected nozzle size and configuration, determinations can be made of the degree of dispersion of a liquid jet formed by the selected nozzle under selected operating conditions of pressure supplied to the nozzle as a function of the length of the jet beam. A channel width and/or width of a longitudinally-oriented opening of the channel can then be selected so that it is at least as great as the measured dispersed jet beam diameter determined in the previous step at the maximum cutting length specified initially. Because, in operation, the presence of the channel will tend to decrease the level of dispersion, the above-mentioned procedure will tend to be conservative.

As mentioned above, while the particular dimensions and parameters should be selected for a particular application based on routine experimentation and optimization, for a variety of embodiments, the following values for various parameters can be typical. For nozzle diameters/nozzle lengths, channel opening effective lengths and jet beam lengths as described above, typical widths of the longitudinally-oriented opening of typical channels can vary from about 0.01 inch to about 0.2 inch, more typically from about 0.01 inch to about 0.08 inch. The ratio of the maximum width of the longitudinally-oriented opening to the effective length of the channel opening typically varies from about 1:4 to about 1:40 or more. Typical values of the maximum width of the longitudinally-oriented opening of the channel divided by the nozzle diameter can range from about 2 to about 30 or more. For embodiments including evacuation lumens and/or connecting sleeves, such as connecting sleeve 12, typical ratios of the maximum cross-sectional dimension of the jet-receiving opening 14 to the maximum width of the interior region of channel 9 at the plane of the jet-receiving opening typically are equal to or exceed unity. Channel width and/or width of the longitudinally-oriented opening of the channel, at the cross section illustrated in FIG. 2D (i.e. at a planar section taken at the downstream end of the jet beam path 20), can range from being about equal to the expanded diameter 25 of the jet beam to exceeding it by a factor of about 4-6 or more. The larger ratios of these dimensions can be advantageous for non-cutting applications, such as lavage applications. Channel height 22 can be advantageously selected, similarly to the above-described channel and longitudinally-oriented opening widths, to be large enough to prevent inadvertent contact between the jet beam and the bottommost surface 6 of the channel during operating conditions where the jet beam is not contacting tissue or other material in the surgical field. In certain embodiments, the channel depth to expanded jet beam diameter (e.g., diameter 25) ratio can vary from between about 1 to about 3 or more.

For embodiments where controlled depth tissue cutting is desirable, as discussed above, it can be advantageous to provide a jet tip having a nozzle positioned, with respect to the channel, such that the jet beam has a positive beam height and passes adjacent to and externally of the channel over at least a portion of its length. In such embodiments, for example such as those illustrated below in FIGS. 11 and 12A-12D, the depth of cut can be a function of, and can in sonic embodiments approximate, the maximum beam height of the jet beam over its length of travel.

In certain embodiments of the invention, one or more geometric and/or functional properties of the jet tip of the invention can be configured to be adjustable by an operator of the inventive surgical instrument, optionally, intraoperatively. Such adjustability can give additional flexibility to the operator in conducting certain medical and surgical procedures.

Figure 3:
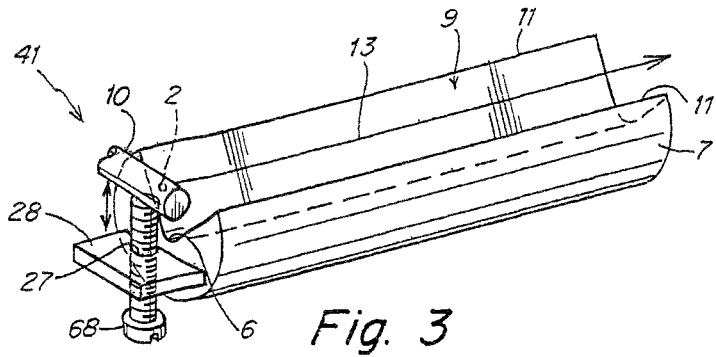
FIG. 3 is a schematic perspective view of an embodiment of a jet tip of a surgical liquid jet instrument having an adjustable beam height according to one embodiment of the invention.
Figure 4:
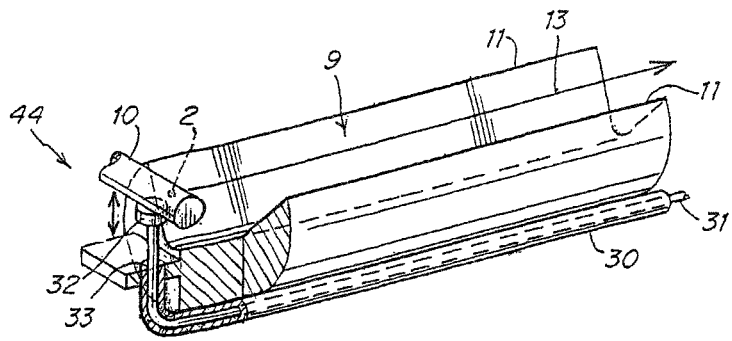
FIG. 4 is a schematic, partially cut-away perspective view of an alternative embodiment of a jet tip of a surgical liquid jet instrument showing a second embodiment for providing an adjustable beam height according to another embodiment of the invention.

In one such embodiment, illustrated in FIGS. 3 and 4, a surgical instrument can be provided with a jet tip allowing the beam height to be varied. In the jet tip embodiment 41 illustrated in FIG. 3, adjustment of the beam height can be effected through the use of the set screw 26 configured to be in contact with, and, alternatively, attached to high pressure lumen 10. Set screw 26 is threaded through a threaded hole 27 in a distal extension 28 of the component 7 forming the channel 9. Set screw 26 acts on high pressure tubing 10 when turned, thereby displacing nozzle 2 with respect to channel 9, thus altering the beam height of jet beam 13. Thus, turning the set screw 26 can increase or decrease the beam height of the jet beam by displacement of the distal end of the high pressure tube. As would be apparent to those of ordinary skill in the art, various other means could alternatively be used to vary the beam height of the jet within or adjacent to the channel, each of which would be within the scope of the present invention.

The jet tip embodiment 44 illustrated in FIG. 4 provides the same functionality but utilizes a mechanism whereby the beam height can be adjusted by an operator of the device intraoperatively during use. In the jet tip 44 of FIG. 4, a tube 30 is provided which carries a wire 31 within its lumen. The wire 31 can be connectable to a handle, lever, knob, slider, or other control element (not shown) located on the body or at the proximal end of the surgical instrument comprising the jet tip of FIG. 4 to facilitate adjustment and control by an operator of the instrument. Such an operator, by adjusting the beam height intraoperatively, could achieve a greater or a lesser degree of cutting or ablation of the tissue worked upon by the jet tip, as desired. The distal end of wire 31 optionally includes a bead or platform 32 thereon, which can prevent it from retracting out of the hole 33 in the distal end of the tube carrying the wire. By pushing on the wire 31, for example by moving a slider or other control element on a handle (not illustrated) of the surgical instrument comprising the jet tip illustrated in FIG. 4, the operator can vary the position of high pressure lumen 10 with respect to the channel, thereby changing the beam height of liquid jet beam 13, thereby changing the cutting/washing activity of the jet tip.

Figure 5A:
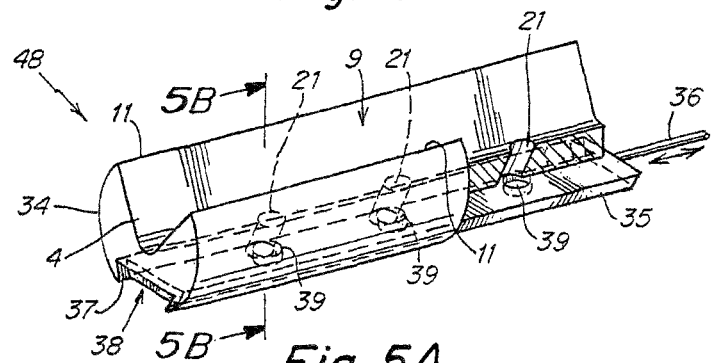
FIG. 5A is a schematic, partially cut-away perspective view of a jet tip of a surgical liquid jet instrument having an adjustable vent aperture according to one embodiment of the invention.
Figure 5B:
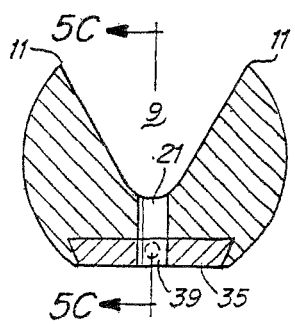
FIG. 5B is a transverse cross-sectional view of the embodiment of FIG. 5A taken along lines 5B-5B.
Figure 5C:
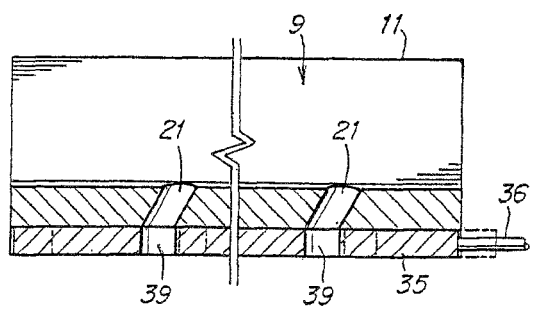
FIG. 5C is a longitudinal cross-sectional view of the embodiment of FIG. 5B taken along lines 5C-5C.

FIGS. 5A-5H illustrate various embodiments of jet tips having adjustable venting for control of the level of suction within the jet-interacting channel during use of certain of the surgical instruments provided by the invention. The channel embodiment 48 illustrated in FIGS. 5A-5C provides manual operator control of the degree of venting, while the channel embodiments illustrated in FIGS. 5E-5H provide for automatic control of venting responsive to the level of suction contained within the interior region of the channel during operation.

Referring to the embodiment illustrated in FIGS. 5A-5C, the jet tip 48 channel 9 illustrated therein allows the total cross-sectional area of the vent apertures providing fluid communication between the interior region of channel 9 and the surrounding environment to be controlled remotely by an operator. Component 34, including channel 9 therein, further includes the sliding cover 35 that can be actuated from the handle or proximal end (not shown) of the device via a wire 36, or, alternatively, a rod or other means. By sliding cover 35 the operator can cover or partially cover some or all of vents 21 in the channel. This can allow for selective control of the force, created by suction, with which the tissue contacting surfaces 11 of the channel are pressed against the tissue, and can, thereby, affect the rapidity and aggressiveness of cutting or lavage produced by the jet tip in operation. Channel-providing component 34 includes an indented slot 37 on its underside 38, sliding plate 35 is connected to a positioning wire 36, which, in turn, is connected to a device (not shown) on the handle or the proximal end of the instrument facilitating control of the position of plate 35 by operator of the instrument. Plate 35 includes holes 39 therein which correspond in number and spacing to vent holes 21 of channel 9. Plate 35 is retained in slot 37 during operation of the device. By moving wire 36, the vent holes can be partially or completely blocked to increase the vacuum force tending to force tissue against tissue contacting surfaces 11 of the channel. In a similar embodiment, not illustrated, a mechanism (not illustrated) could be adapted to similarly vary the open area of the entrance aperture 4 of channel 9 so as to increase or decrease the venting effect produced by the open area of such aperture during operation.

Figure 5D:
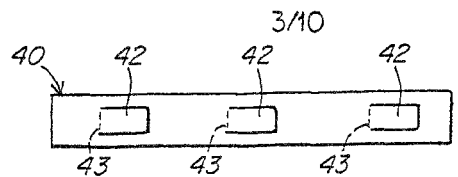
FIG. 5D is a top plan view of an automatic pressure relief insert according to one embodiment of the invention.
Figure 5E:
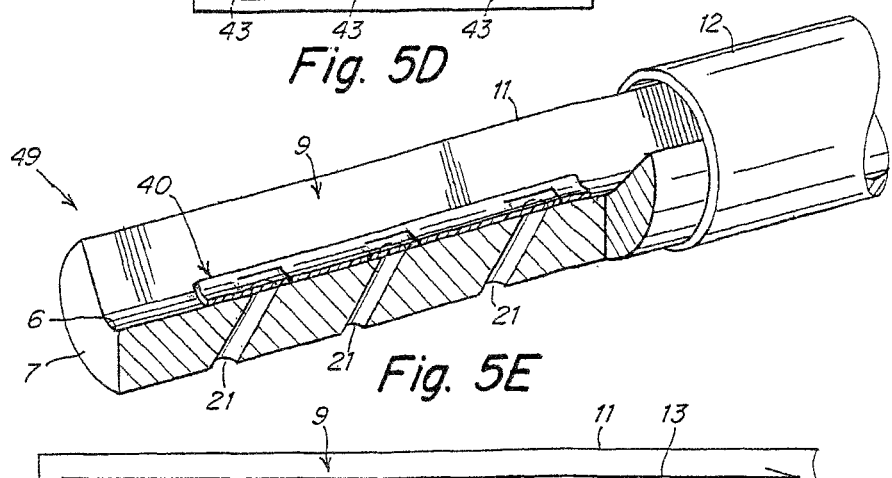
FIG. 5E is a schematic, partially cut-away perspective view of a portion of an embodiment of a jet tip including a channel containing the automatic pressure relief insert of FIG. 5D.
Figure 5F:
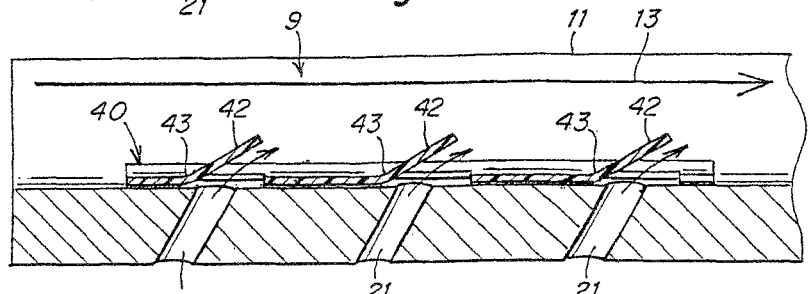
FIG. 5F is a longitudinal cross-sectional view of the embodiment of FIG. 5E showing the pressure relief valves of the insert in an open configuration.

FIGS. 5D-5F illustrate a first embodiment for providing automatic control of vent aperture open area responsive to a level of suction within the interior region of channel 9 during operation of the surgical instrument comprising the jet tip 49. As illustrated, channel-providing component 7, which is essentially identical to that illustrated previously in FIG. 2B, includes at a position adjacent to and in contact with bottommost surface 6 of the interior of the channel an insert 40. Insert 40 can comprise a strip constructed of a resilient material, e.g., a resilient plastic material, including a plurality of pressure relief ports 42 formed within the insert. Pressure relief ports 42 comprise flaps cut through the thickness of insert 40 on three sides and which include a hinge area 43 comprising that portion of the flap material still integral with the remainder of insert 40. Pressure relief ports 42 correspond in number and spacing to vent holes 21 of channel 9. Insert 40 is secured to the bottommost surface 6 of channel 9 such that the pressure relief ports overlay the vent holes. Insert 40 can be attached to surface 6 in a variety of ways apparent to those of ordinary skill in the art. In one particular embodiment, the insert is attached to the surface an adhesive.

The material and thickness of insert 40 can be selected such that the flaps 42 overlaying the vent hole require a certain, desirable level of force to be displaced by a given amount. Thus, by selecting particular materials and thicknesses, the responsiveness of the change of open area of the vent apertures to suction pressure within the channel can be selected. As illustrated in FIGS. 5E and 5F, pressure relief ports 42, when the suction level within the internal region of channel 9 is below a particular threshold are biased in the closed position inhibiting fluid communication through apertures 21. However, as shown in FIG. 5F, when a level of suction created by passage of jet stream 13 exceeds a certain threshold value, the force tending to open ports 42 will exceed the force required to bend the flaps at their hinge region 43 such that the flaps will open facilitating fluid communication through vent apertures 21 into the interior region of the channel, thereby tending to maintain suction level within the channel within a desired range.

Figure 5G:
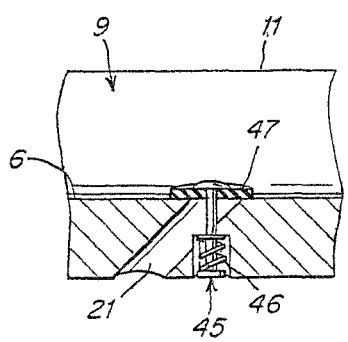
FIG. 5G is a fragmentary longitudinal cross-sectional view of another embodiment of a channel of a jet tip with a second embodiment for providing automatic pressure relief valves showing a pressure relief valve in a closed configuration.
Figure 5H:
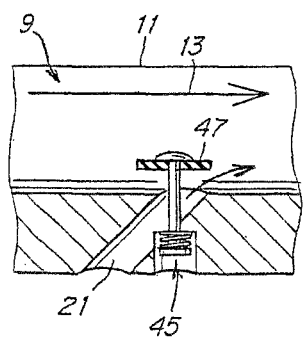
FIG. 5H is a fragmentary longitudinal cross-sectional view of the embodiment of FIG. 5G showing the pressure relief valve in a closed configuration.

An alternative embodiment for effecting essentially the same functionality is illustrated in FIGS. 5G and 5H. In this embodiment, instead of providing a resilient insert having a plurality of pressure relief ports therein, as described above, a plurality of spring loaded pressure relief valves 45 are provided (one per vent aperture 21). Spring loaded pressure relief valves 45 comprise a spring or other biasing element 46 biasing a sealing element 47, comprised of rubber or other resilient material, closed against bottommost surface 6 of the interior region of channel 9. When, as illustrated in FIG. 5H, the suction level inside the channel exceeds that required to overcome the force generated by biasing element 46, the pressure relief valve 45 will open allowing fluid communication between the surrounding environment and the interior region of channel 9 through vent aperture 21.

In certain embodiments, surgical instruments provided according to the invention can be configured so that the jet-interacting channel is contained within a channel-providing insert that can be removed and replaced by an operator of the instrument with another insert having a differently configured channel therein. In one such embodiment, the channel could be formed in a component similar to components 7 illustrated above, which component is not permanently affixed to sleeve 12, so that it can be removed and replaced with a similar component having a different channel shape, size, etc., thereby providing a different balance of instrument properties. For example, in one such application, after cutting damaged tissue utilizing an insert having one type of channel therein, an insert having different type of channel could be substituted to facilitate rapid and thorough lavage of the previously treated area. Replacement channel-providing components could, in one embodiment, be simply slipped into the sleeve and retained in place by high pressure lumen 10, or, alternatively, could be secured by a clip or other securing element. For certain embodiments where the channel is provided in a component formed of a sheet of metal, such component could be compressed slightly during insertion of the component into the sleeve element, and held in place in the sleeve by the natural spring action of the metal sheet.

FIGS. 6A-6D illustrate an embodiment of a jet tip 58 including a jet-interacting channel having a cross-sectional shape that can be adjusted by an operator of the instrument during use of the device, optionally intraoperatively. The sides of channel 50 as illustrated are provided by moveable leaves 51 and 52, and the angle 59 between the leaves may be varied by sliding channel-providing component 53 longitudinally within trolley 61 via wire/rod 65. Channel-providing component 53 is separated from sleeve 12 by an adapter element 54. The adapter element includes slot 55 on each side, in which a pin elements 56 and 57, attached to the downstream end of leaves 51 and 52, respectively, slide. Leaves 51 and 52 form the sides of channel 50. Each sleeve, as noted above, includes a pin at its distalmost end which interact with slots 55. Each sleeve is pivotally connected to carrier 53 by a hinge 60. Leaves 51 and 52 can be secured within carrier 53 via end plates 62 and 63, or by any other suitable means of securing the hinge, as would be apparent to those of ordinary skill in the art. Carrier 53 is moved longitudinally within trolley 61 via pushing or pulling of wire/rod 65, the angle 59 between the leaves is changed by the movement of pins 56 and 57 within slanted slots 55 of adapter 54, thereby changing the shape of channel 50. As illustrated, trolley 61 includes on its underside a slot 64 through which high pressure lumen 10 (not shown) passes when the jet tip is assembled in an operative configuration. As carrier 53 is made to move back and forth longitudinally within trolley 61, high pressure lumen 10, which can be connected to plate 62, will slide back and forth within slot 64, thereby maintaining a consistent spacing between the jet nozzle and inlet aperture 66 of channel 50. It should be understood that the particular embodiment illustrated in FIGS. 6A-6D is only one of many possible embodiments and mechanisms which could be utilized to facilitate user adjustment of the shape and/or width of the jet-interacting channel of a jet tip according to the invention. Those of ordinary skill in the art will readily conceive of various additional ways of effecting the same or similar configurational changes of the channel utilizing other mechanisms and mechanical schemes apparent to those of ordinary skill in the art. Such variations and modifications are deemed to be within the scope of the present invention as defined by the appended claims.

FIGS. 7A and 7B illustrate one embodiment of an assembled surgical handpiece instrument 70 having a distal end 72 containing one embodiment of a jet tip 74 provided according to the invention. Jet tip 74 comprises the distal end of high pressure lumen 10, channel-forming component 7 including channel 9 therein, and connecting sleeve 12 at the distal end of evacuation lumen 16 connecting the evacuation lumen in fluid communication with channel 9. Tissue to be treated with the surgical handpiece is denoted at 76. High pressure lumen 10 and evacuation lumen 16 enter handpiece body 78, which, in the illustrated embodiment, comprises two mated sections 80 and 82. In certain embodiments, body 78 need not be pressure-tight (i.e., it need not sustain internal pressure). In such embodiments, body 78 can advantageously include slots or other openings connecting the inside of the body to the surrounding atmosphere to facilitate sterilization of the internal components within the body. Components 80 and 82 of handpiece body 78 can be connected together by any convenient means apparent to those of ordinary skill in the art such as including, but not limited to, screw connectors, tab-in-slot connectors, adhesives, etc.

Two tubes emerge from the proximal end 84 of the handpiece body: a low pressure evacuation tube 86 and a flexible high pressure hose 88, each of which can be made of a variety of suitable materials as would be apparent to those of ordinary skill in the art. In one particular embodiment, each of the above-mentioned tubes is made of a suitable polymeric material. Connections within body 78 facilitating fluid communication between high pressure lumen 10 and flexible high pressure hose 88 and between evacuation lumen 16 and low pressure evacuation tube 86 are illustrated in FIG. 7B. While, in the illustrated embodiment, high pressure connection 90 and a low pressure connector 92 are located within handpiece body 78, in alternative embodiments, the connections can be made either proximally or distally of the handpiece body. In yet other embodiments, high pressure lumen 10 and/or evacuation lumen 16 may simply be provided having a length sufficient to extend completely through handpiece body 78 and, alternatively, proximately thereof, such that a separate high pressure line and suction tube need not be provided. High pressure connection 90 can comprise a wide variety of suitable high pressure fittings rated to withstand applied operating pressures, which connections are well known to those skilled in the art and are described in greater detail in Applicants' U.S. Pat. No. 6,375,635 (as are appropriate materials for forming various components of the handpiece 70). Similarly, low pressure connector 92 can be any of a wide variety of suitable tubing connectors well known to those of ordinary skill in the art and described in the above-mentioned U.S. patent.

High pressure hose 88 is connected to a source of pressurized liquid (e.g., a high pressure pump—not shown). Evacuation tube 86 can be connected to a suitable container for containing and storing recovered fluid and debris and, optionally, containing a filtered outlet for entrained air (not shown). For embodiments wherein the surgical handpiece requires or utilizes a source of external suction to facilitate evacuation, evacuation tube 86 can be connected in fluid communication with a suitable source of suction, such as a vacuum pump, aspirator, house vacuum line, etc.

FIGS. 8A-8E illustrate various views of two exemplary embodiments of channel-providing inserts provided according to the invention. The particular configuration and dimensions illustrated and recited below are exemplary of one particular embodiment provided for illustrative purposes. As described above, particular configurations and parameters can be varied and should be determined by routine experimentation and optimization based upon the particular desired operating characteristics of the instrument, as would be apparent to those of ordinary skill in the art.

Figure 8A:
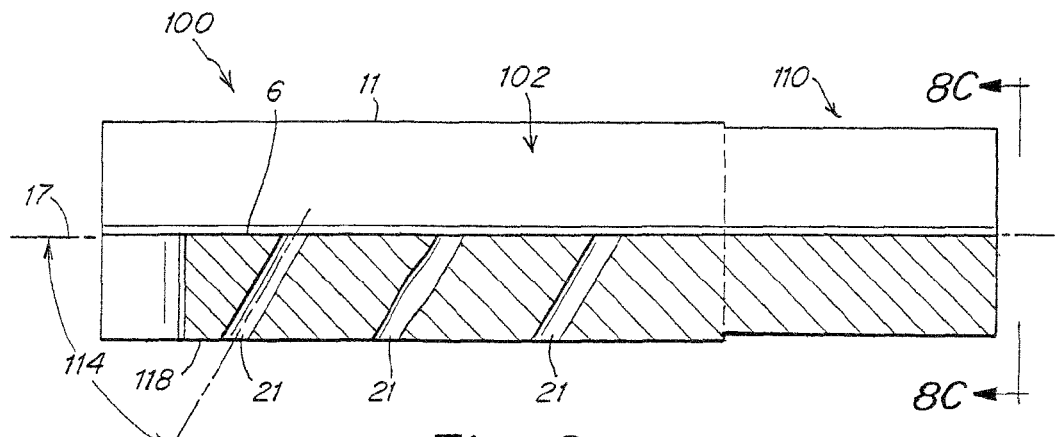
FIG. 8A is a longitudinal cross-sectional view of a channel-providing component of a jet tip according to one embodiment of the invention.
Figure 8B:
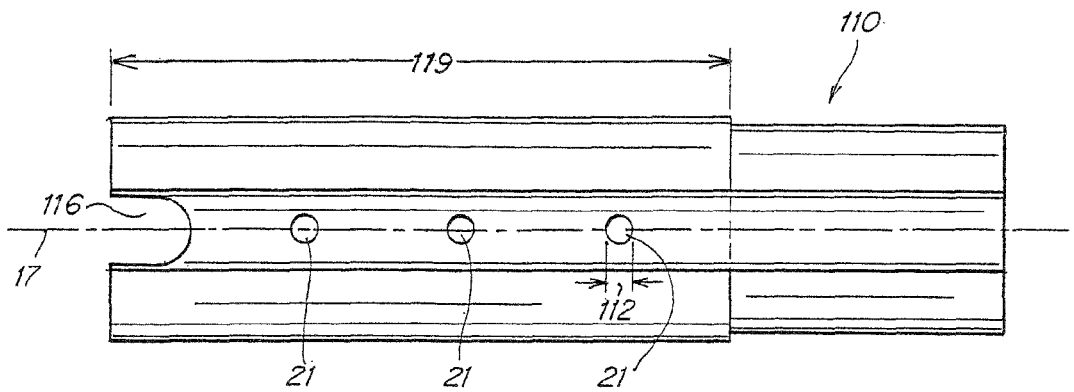
FIG. 8B is a top plan view of the channel-providing component of FIG. 8A.
Figure 8C:
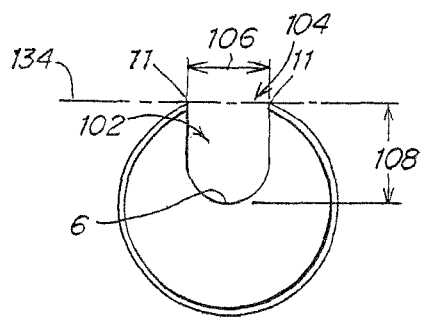
FIG. 8C is an end view of the channel-providing component of FIG. 8A, as viewed from the right of FIG. 8B.

Referring to FIGS. 8A-8C, the illustrated channel-providing insert 100 includes a "U" shaped channel 102 therein. The channel 102 includes a longitudinally-oriented opening 104, extending along the entire length of the channel, having a width 106 of about 0.06 inch. Channel depth 108 is about 0.075 inch. Downstream end 110 of the insert has been provided with a reduced diameter to facilitate a slip fit into a connecting sleeve (not shown), such as connecting sleeve 12 illustrated previously. Three vent aperture holes 21 having a diameter 112 of about 0.02 inch have been drilled in insert 100 at an angle 114 of about 60° with respect to longitudinal axis 17 of channel 102. Also provided is a notch 116 at the downstream, distal end of the channel to accommodate passage of the high pressure lumen (not shown), which, in the illustrated embodiment, would enter the channel through the bottom 118 of the insert. In the illustrated embodiment, width 106 of the longitudinally-oriented opening 104 of channel 102 remains essentially constant over the effective length 118 of the longitudinally-oriented opening 104 of channel 102, when the insert is assembled in an operative configuration in a jet tip.

Figure 8D:
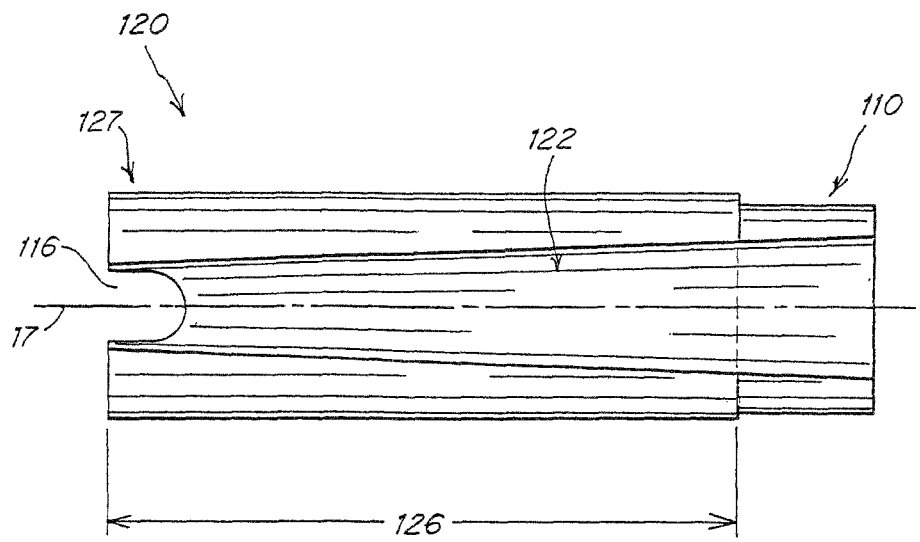
FIG. 8D is a top plan view of a channel-providing component of a jet tip according to another embodiment of the invention.
Figure 8E:
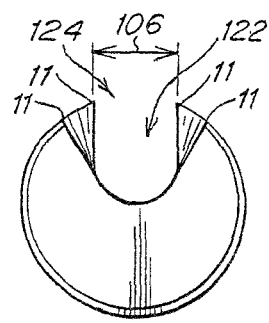
FIG. 8E is an end view of the channel-providing component of FIG. 8D, as viewed from the right.

FIGS. 8D and 8E illustrate an embodiment of a channel-providing insert 120 including therein a channel 122 with a longitudinally-oriented opening 124 having a width that increases along its length. Such an embodiment can be advantageous for instruments utilizing jet tips having nozzles forming liquid jets which tend to disperse more substantially over the effective length 126 of the longitudinally-oriented opening 124 of the channel 122. In such embodiments, having a channel with a longitudinally-oriented opening that expands from the jet inlet along the length of travel of the jet beam can tend to prevent undesirable contact of the expanded, dispersed jet beam with the walls of the channel and can also tend to increase the level of uniformity of air/liquid influx and aspiration into the channel along the length of the longitudinally-oriented opening of the channel. As illustrated, and as shown most clearly in FIG. 8E, channel 122, at its upstream end 127, which would be adjacent to the nozzle in operation, has a "U"-shaped trough formed therein similar in shape and dimensions to that illustrated previously for the embodiment or FIG. 8C. As one moves along the channel towards the direction of reduced diameter proximal portion 110, the width of the longitudinally-oriented opening 124 expands and the channel cross-sectional dimension gradually becomes that of a "V" having a rounded bottom, as illustrated previously in the embodiment shown in FIGS. 2C and 2D.

FIGS. 9A-9E illustrate alternative shapes for jet-interacting channels and channel-providing components, as viewed in cross sections taken in a plane perpendicular to the longitudinal axis of such channels. The illustrated channels exemplify various profiles that can be provided by channel-providing inserts formed via shaping a sheet of metal, or other material, according to certain embodiments of the invention. The asymmetric designs, i.e. FIGS. 9B, 9C and 9E, are configured to vary the action and aggressiveness of jet beam 13 as the channel is moved laterally across tissue to be treated. For embodiments of jet tips including such asymmetric channels, the appropriate beam height would be measured as the distance 130 measured along a normal line 132 separating the center line of jet beam 13 from a plane 134 tangent to tissue-contacting surfaces 11 of the channels. For example, the beam height of the embodiment illustrated in FIG. 9B is somewhat negative (i.e., the center line of the jet beam falls on the channel side of plane 134), while the beam heights for the asymmetric designs in FIGS. 9C and 9E are approximately 0.

FIGS. 9D and 9E illustrate embodiments of channel-providing components including "extended" tissue contacting surfaces 136. Such surfaces can advantageously be employed to help "smooth out" soft tissue, such as skin, during techniques such as dermabrasion, to make the depth of cut or ablation of the tissue more consistent and to facilitate smoother, more controllable gliding of the channel across the surface of the tissue during operation.

The "C" configuration illustrated in FIG. 9A, while generally less desirable for configurations involving positive beam heights and tissue cutting, can be advantageously utilized for embodiments involving negative beam heights, as illustrated, especially for applications involving washing/lavage of tissue.

FIG. 10A illustrates an embodiment of a jet tip 137 providing an open area 4 at the entrance aperture at the distal end of channel 9 forming a vent aperture when the jet tip is in operation. The cross-sectional open area of the vent aperture thus formed can be adjusted, in such embodiments, by selectively spacing high pressure lumen 10 with respect to the inlet of channel 9 so as to occlude a desirable fraction of the cross-section area of the inlet of channel 9 by the high pressure lumen. Alternatively, the high pressure lumen, at its distal end, can be shaped or sized relative to the inlet of the channel to, similarly, provide a desirable degree of open area for forming a vent aperture. In some embodiments, providing a vent aperture comprising at least a portion of an inlet area of the channel, as illustrated in FIG. 10A (and below in FIG. 10B) can be particularly desirable because fluid entrained into the channel through the vent aperture, in such embodiments, may have a tendency to surround the jet beam more effectively, which can lead to less hydrodynamic disturbance of the jet beam along its length, in certain situations, than may be the case for embodiments including vent apertures positioned farther downstream within the channel and along the length of the jet beam.

FIG. 10B illustrates an alternative embodiment 139 in which the distal end 138 of channel 9 is flared outwardly in a region surrounding and/or adjacent to high pressure lumen 10 to create a larger open area 4 at the inlet of the channel providing a vent aperture. In general, for all embodiments providing vent apertures, for reduction or minimization of "sticking," during use, total open area of the vent apertures provided can vary from about less than 1% to about 150% of the total open area of the longitudinally-oriented opening of the channel, which can be occluded by tissue during use of the instruments. More typically, the vent aperture area will fall within the range of from about 1% to about 40%, more typically from about 2% to about 10%, and in one embodiment the open area of the vent apertures is about 4% of the total open area of the tissue-contacting portion of the longitudinally-oriented open area of the channel. While the above-values provide certain guidelines for selecting appropriate vent aperture sizes, it should be understood that the total aperture area needed to produce a desired surgical effect would be a function of not only the vent aperture area and the area of the longitudinally-oriented opening of the channel, but also the tendency of the jet tip to create hydrodynamic suction, which is a function of various factors including the pressure of the fluid supplied to the nozzle, the size and shape of the nozzle, the shape and cross-sectional area of the jet-interacting channel, etc., as would be apparent to those skilled in the art. Accordingly, appropriate vent aperture sizes and configurations should be selected for particular applications via routine screening tests, experiments and routine optimization.

Figure 11:
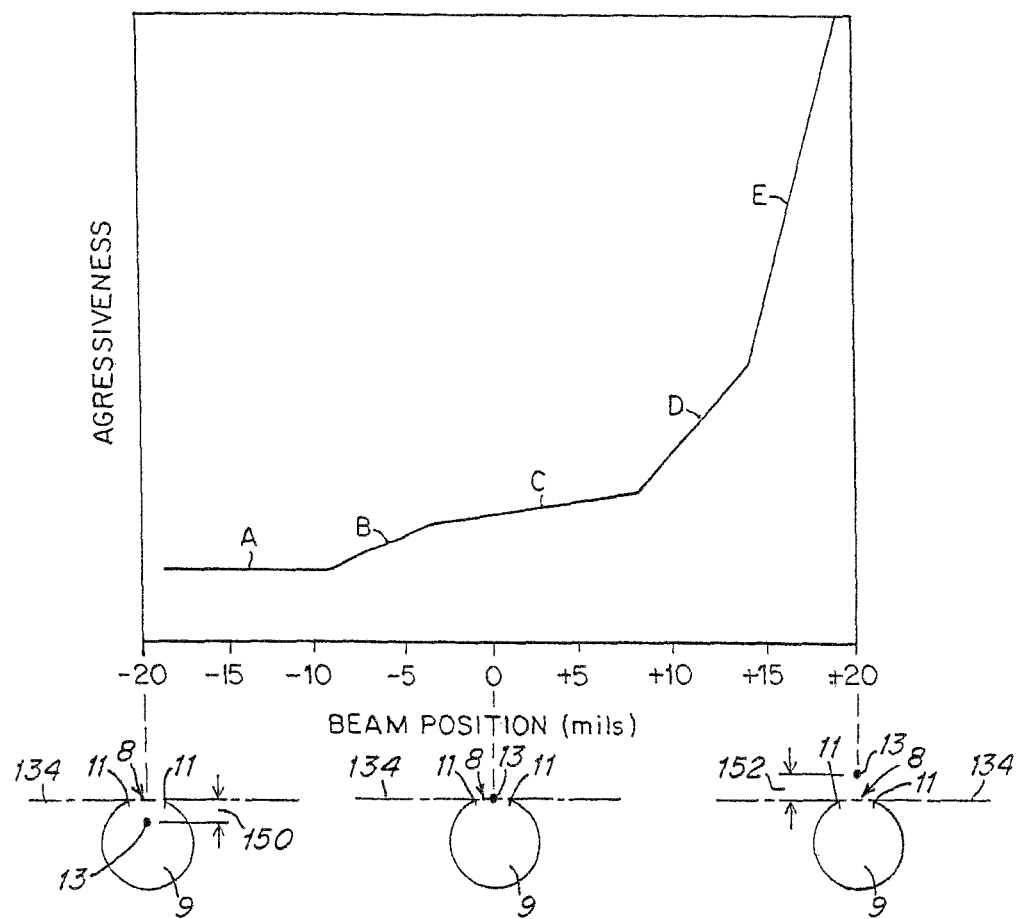
FIG. 11 is a graph plotting tissue removal aggressiveness (Y-axis) as a function of beam height (X-axis) for a surgical instrument having a jet tip with a channel having a transverse cross-sectional shape as illustrated schematically at the bottom the figure.

FIG. 11 illustrates one example of actual experimental results of tissue treatment utilizing a surgical instrument having a jet tip with a jet-interacting channel provided according to an embodiment of the invention. The experimental results illustrate a relationship between the beam height to the depth of cutting/ablation of tissue with the jet tip and, in general, the degree of aggressiveness of tissue removal with the jet tip as a function of beam height. The jet tip utilized had a configuration similar to that illustrated previously in FIG. 10A, except that the channel was configured to have a cross-sectional shape similar to that illustrated previously in FIG. 9A. The bottom portion of FIG. 11 illustrates, schematically, a cross-section of the "C" shaped channel utilized. The channel comprised a section of metal tubing open at the distal and proximal ends and including a rectangularly-shaped longitudinally-oriented opening running the entire effective length of the channel, which was formed in the sidewall of the tubing. The channel had a maximum diameter of the interior region of about 0.095 inch, and had a longitudinally-oriented opening 8 with a width of about 0.031 inch. The tissue utilized in the experiment comprised an animal muscle tissue, such as chicken breast tissue.

The jet tip also included a high pressure lumen having a 0.005 inch I.D. nozzle therein. The nozzle had a nozzle length of about 0.02 inch and comprised a necked-down region of the distal end of metal tubing. The graph shows the aggressiveness of tissue removal of the jet tip (Y axis) as a function of the beam height (in mils=thousandths of an inch) (X axis). "Aggressiveness" was quantified as the quantity (in grams) of muscle tissue removed per minute by the jet tip during operation.

The position of the jet nozzle and, thereby, the beam height was manually adjusted over the range indicated by the graph. Positions of the center line of the jet beam located within the channel and below the plane 134 of the longitudinally-oriented opening of the channel (as shown in FIG. 11, bottom left) comprised negative beam heights, i.e., distances 150 below the plane 134 of the longitudinally-oriented opening of the channel. FIG. 11, bottom center, shows a configuration where the center line of the jet beam is positioned with a beam height of 0. FIG. 11, bottom right, illustrates a configuration wherein the center line of the jet beam is positioned adjacent to the longitudinally-oriented opening 8 and externally of the channel at a positive beam height 152. In general, for configurations employing positive beam heights such as shown in FIG. 11, bottom right, the depth of cut and/or ablation of tissue is proportional to the positive distance between the tissue-contacting portion of the longitudinally-oriented opening and the centerline of the jet beam and, in certain situations, can be approximately equal thereto.

As shown in the graph, for beam heights ranging between −0.02 inch to about −0.01 inch there was negligible cutting action (region A). Such a regime would be indicative of a jet tip providing washing/lavage action of tissue without substantial tissue removal. For a beam height within the range of about −0.01 inch to about −0.003 inch, the jet beam rapidly became more aggressive (region B). In the region of from about −0.003 inch to about 0.008 inch, aggressiveness in tissue removal depth rose smoothly and predictably with beam height (region C). Beyond 0.08 inch, aggressiveness and tissue cutting depth rose rapidly (indicated by regions D and E). Testing similar to that described above can also be easily applied to other designs and configurations described herein and can be part of the routine experimentation and optimization that can be utilized to select particular dimensions, configurations, parameters, etc. as discussed above.

FIGS. 12A-12D illustrate an alternative embodiment of the surgical handpiece instrument illustrated above in FIGS. 7A-7B, including a distal end 160 having a jet tip 162 in which both the nozzle and jet beam-interacting channel are formed as a single piece. In addition, as illustrated most clearly in FIG. 12D, this embodiment utilizes a jet tip having a nozzle 164 having a centerline located externally of the channel 166 and separated from the tissue-contacting surface 168 of the channel adjacent the longitudinally-oriented opening 170 of the channel by a distance 172, which distance defines the beam height of jet beam 174 as measured at the plane of the jet opening of nozzle 164. In one particular embodiment, distance 172 can be approximately 0.02 inch enabling the jet tip to slice off, ablate, and/or plane thin layers of tissue of a similar thickness.

In addition, to facilitate collection of the liquid comprising jet beam 174 while reducing the necessary outer diameter of the distal end 180 of the evacuation lumen and the overhang 182, the centerline of nozzle 164 is configured such that it is directed along a first direction that is essentially parallel to a projection of the longitudinal axis of channel 166 on a plane co-planar with the longitudinally-oriented opening 170 of the channel. In other words, referring to the orientation illustrated in FIG. 12D, nozzle 164 is angled upwardly with respect to the longitudinal axis of channel 166 such that the jet beam 174 passes adjacent to and externally of a first portion 184 of the longitudinally-oriented opening 170 of channel 166 and, downstream of first portion 184, passes within channel 166. In alternative embodiments, in which centerline of nozzle 164 is essentially parallel to the longitudinal axis of the channel in all planes of measurement, the jet beam formed by the nozzle would not, when the jet beam is not encountering tissue in the operating field, tend to enter the channel but would, rather, pass adjacent to, externally of, and along essentially the entire effective length of the longitudinally-oriented opening of the channel, when the instrument is in operation.

In addition to facilitating collection of the liquid comprising the liquid jet beam with reduced or essentially no overhang 182 of the jet-receiving opening of the evacuation lumen of the jet tip, the illustrated configuration, utilizing an upwardly angled nozzle, also can provide two discrete regions of functionality of the jet beam along the jet length. In region 184, the jet beam is characterized by a positive beam height and facilitates controlled-depth cutting/ablation of tissue. Downstream of this region, the jet beam, once it enters channel 166, will tend to become less aggressive to tissue and can facilitate washing/lavage of the tissue area previously cut/ablated by the jet beam in region 184.

In addition, in some particular embodiments, in order to facilitate use of the instrument, or previously illustrated instruments/jet tips, on tissue surfaces having natural curvature, jet tip 162 can include a channel 166 with tissue-contacting surface 168 that are somewhat arcuate when viewed in the cross-sectional plane illustrated in FIG. 12D. Such embodiments can provide, in some instances, improved and/or additional functionality for treating curved internal surfaces, for example certain bone surfaces, and/or curved external surfaces, for example certain naturally curved body parts such as fingers, toes, etc. For embodiments such as that illustrated in FIGS. 12A-12D that include nozzles directed at an angle such that the liquid jet formed by the nozzle is separated from a bottommost portion 208 of the channel by an amount that decreases along the length of the channel, the angle between the centerline of the nozzle and the longitudinal axis of the channel can, for certain embodiments, typically range from between about 1 degree to about 20 degrees, and in certain embodiments between about 3 degrees and about 15 degrees.

Jet-interacting channel 166 of jet tip 162 also includes two vent apertures 179 therein positioned on each side of channel 166. High pressure tube 110 enters distal nozzle-forming component 186 at inlet 188. At its proximal end, channel 166 is connected in a fluid communication with sleeve/evacuation lumen 192. To enhance evacuation efficiency in the illustrated embodiment, channel 166 includes a proximal-most region 194 having an increased internal diameter providing an area of expansion adjacent the distal end of the evacuation lumen where it connects to the channel.

As illustrated most clearly in FIG. 12B, channel 166 has a "U" shaped cross-sectional configuration. In alternative embodiments, as discussed previously, channel 166 can have different shapes. In one particular embodiment, channel 166 has a cross-sectional shape that is rectangular.

Referring again to FIG. 12D, jet tube 110 communicates with an entry 196 in distal nozzle-forming component 186, which, in turn, is in fluid communication with a thin chamber 198 oriented perpendicularly to the longitudinal axis of channel 166. Chamber 198 can be formed, in an exemplary embodiment, by brazing an end plate 200 in a recess 202 formed within the distal end of the component 204 forming channel 166. Nozzle 164 can advantageously be formed in a protrusion 206 of component 204 prior to attaching end plate 200.

As discussed above, during operation, initially, jet beam 174 is positioned externally of channel 166, and spaced apart from edges 168 of which would contact the tissue (not shown) during use of a surgical instrument comprising the jet tip during a surgical procedure. However, as the jet beam progresses along the channel, it angles upwards towards the bottommost surface 208 of channel 166 and, typically, broadens somewhat due to dispersion. Upon entry into sleeve 192, in some embodiments, the expanded jet beam can occupy a substantial fraction (as discussed above) of the area of the jet-receiving opening of sleeve 192. As indicated in the illustrated embodiment, vent apertures 179 are positioned above jet beam 174 and at the distal end of channel 166. This configuration can, under certain conditions, facilitate maintenance of the trajectory of the jet beam along the projection of the centerline of nozzle 164. In one particular exemplary embodiment, a depth 210 of channel 166 is about 0.08 inch, the width of the longitudinally-oriented opening 170 of channel 166 is about 0.04 inch, and the beam height measured at the plane of the jet opening of nozzle 164, as mentioned above, is about 0.02 inch.

While several embodiments of the invention have been described and illustrated herein, those of ordinary skill in the art will readily envision a variety of other means and structures for performing the functions and/or obtaining the results or advantages described herein, and each of such variations or modifications is deemed to be within the scope of the present invention. More generally, those skilled in the art would readily appreciate that all parameters, dimensions, materials, and configurations described herein are meant to be exemplary and that actual parameters, dimensions, materials, and configurations will depend upon specific applications for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described. The present invention is directed to each individual feature, system, material and/or method described herein. In addition, any combination of two or more such features, systems, materials and/or methods, provided that such features, systems, materials and/or methods are not mutually inconsistent, is included within the scope of the present invention. In the claims (as well as in the specification above), all transitional phrases or phrases of inclusion, such as "comprising," "including," "carrying," "having," "containing," "composed of," "made of," "formed of" and the like shall be interpreted to be open-ended, i.e. to mean "including but not limited to." Only the transitional phrases or phrases of inclusion "consisting of" and "consisting essentially of" are to be interpreted as closed or semi-closed phrases, respectively.

The invention claimed is:

1. A surgical instrument comprising:
   a distal end adapted to perform a surgical procedure on a patient and a proximal end;
   a pressure lumen configured and positioned to conduct a liquid from the proximal end towards the distal end of the instrument;
   a nozzle in fluid communication with the pressure lumen that is shaped to form a liquid jet as the liquid flows therethrough;
   a channel, having a depth and a length, the length being defined along a longitudinal axis of the channel, the channel including a tissue-contacting portion including a longitudinally-oriented opening to a surrounding environment extending along at least a portion of the length of the channel, the longitudinally-oriented opening having a total effective length, as measured along the length of the channel, and a width, as measured in a direction perpendicular to the longitudinal axis of the channel, wherein the total effective length of the longitudinally-oriented opening is greater than the width of the longitudinally-oriented opening; and
   at least one vent aperture in the channel configured and positioned to provide fluid communication between an interior region of the channel and the surrounding environment when the longitudinally-oriented opening of the tissue-contacting portion of the channel is occluded, the vent aperture being configured and positioned to act as a suction break to reduce the level of suction created within the interior region of the channel, wherein
   the channel is positioned adjacent to and downstream of the nozzle such that the liquid jet, over at least a portion of its length, passes at least one of within the channel and adjacent to the channel, and also passes along a length of at least a portion of the longitudinally-oriented opening of the channel, when the instrument is in operation; and
   an evacuation lumen comprising a jet-receiving opening that is separate and distinct from the vent aperture and that is located opposite a jet opening of the nozzle and adjacent to and downstream of the channel, wherein the evacuation lumen is constructed and positioned to enable it to collect liquid comprising the liquid jet formed by the nozzle, when the instrument is in operation.

2. The surgical instrument as in claim 1, wherein a downstream end of the channel is connected in fluid communication with the jet-receiving opening of the evacuation lumen.

3. The surgical instrument as in claim 2, wherein the downstream end of the channel is connected to the evacuation lumen by a sleeve element.

4. The surgical instrument as in claim 2, wherein the evacuation lumen is shaped and positionable to enable evacuation of essentially all of the liquid comprising the liquid jet from the jet-receiving opening to the proximal end of the instrument, without the need for an external source of suction.

5. The surgical instrument as in claim 1, wherein the at least one vent aperture comprises an inlet opening at an upstream end of the channel.

6. The surgical instrument as in claim 1, wherein the at least one vent aperture comprises at least one vent hole positioned at a location along the length of the channel.

7. The surgical instrument as in claim 1, wherein the at least one vent aperture comprises at least one indentation in a tissue-contacting surface of the tissue-contacting portion of the channel.

8. The surgical instrument as in claim 1, wherein a total cross sectional area of the at least one vent aperture is between about 2% and about 150% of the total area of the longitudinally oriented opening of the channel.

9. The surgical instrument as in claim 8, wherein the total cross sectional area of the at least one vent aperture is between about 2% and about 40% of the total area of the longitudinally oriented opening of the channel.

10. The surgical instrument as in claim 9, wherein the total cross sectional area of the at least one vent aperture is between about 2% and about 10% of the total area of the longitudinally oriented opening of the channel.

11. The surgical instrument as in claim 10, wherein the total cross sectional area of the at least one vent aperture is about 4% of the total area of the longitudinally-oriented opening of the channel.

12. The surgical instrument as in claim 8, wherein the total open area of the at least one vent aperture is adjustable by an operator of the surgical instrument.

13. The surgical instrument as in claim 12, wherein the total open area of the at least one vent aperture can be varied intraoperatively.

14. The surgical instrument as in claim 8, wherein the total open area of the at least one vent aperture is configured to be automatically adjustable based on a level of suction present within the interior region of the channel during operation of the surgical instrument.

* * * * *